(12) United States Patent
Nguyen et al.

(10) Patent No.: US 10,478,055 B2
(45) Date of Patent: Nov. 19, 2019

(54) MULTI-PORT CAP FOR REAGENT CONTAINER

(71) Applicant: ASP Global Manufacturing GmbH, Schaffhausen (CH)

(72) Inventors: Nick N. Nguyen, Silverado, CA (US); Yan Fang, Irvine, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 128 days.

(21) Appl. No.: 15/252,550

(22) Filed: Aug. 31, 2016

(65) Prior Publication Data

US 2018/0055349 A1   Mar. 1, 2018

(51) Int. Cl.

| | |
|---|---|
| *A61B 1/12* | (2006.01) |
| *B08B 3/08* | (2006.01) |
| *A61L 2/18* | (2006.01) |
| *A61L 2/24* | (2006.01) |
| *A61B 90/70* | (2016.01) |

(52) U.S. Cl.
CPC .............. *A61B 1/123* (2013.01); *A61B 1/125* (2013.01); *A61L 2/18* (2013.01); *A61L 2/24* (2013.01); *B08B 3/08* (2013.01); *A61B 2090/701* (2016.02); *A61L 2202/17* (2013.01); *A61L 2202/24* (2013.01)

(58) Field of Classification Search
None
See application file for complete search history.

(56) References Cited

U.S. PATENT DOCUMENTS 5,711,921 A * 1/1998 Langford ............... A61B 1/123
                                                134/169 R
6,986,736 B2    1/2006 Williams et al.
(Continued)

FOREIGN PATENT DOCUMENTS

| EP | 1644051 B1 | 1/2008 |
| EP | 3032246 A1 | 6/2016 |
| JP | 2010-057752 A | 3/2010 |

OTHER PUBLICATIONS

U.S. Appl. No. 15/157,800, filed May 18, 2016.
U.S. Appl. No. 15/157,952, filed May 18, 2016.

*Primary Examiner* — Jason Y Ko
*Assistant Examiner* — Cristi J Tate-Sims
(74) *Attorney, Agent, or Firm* — Frost Brown Todd

(57) ABSTRACT

A liquid distribution system is configured to deliver a disinfectant solution to a medical device within an enclosure. A disinfectant concentration measuring subsystem includes a mixing chamber, a reservoir, a reservoir cap, a pump, and a concentration analysis assembly. The first mixing chamber is in fluid communication with an outlet of the liquid distribution system. The reservoir is configured to contain a reagent solution and is in fluid communication with the mixing chamber. The reservoir cap includes a static member, which is configured to couple with a supply conduit and a return conduit; and a rotating member, which is configured to rotate relative to the static member to couple the reservoir cap with the reservoir. The pump is configured to simultaneously pump the disinfectant solution and the reagent solution into the mixing chamber. The concentration analysis assembly is operable to determine a concentration of disinfectant output from the mixing chamber.

19 Claims, 15 Drawing Sheets

(56) References Cited

U.S. PATENT DOCUMENTS

| | | | |
|---|---|---|---|
| 7,329,250 B2 * | 2/2008 | Romano | A61M 1/0001 141/18 |
| 7,479,257 B2 | 1/2009 | Nguyen et al. | |
| 7,686,761 B2 | 3/2010 | Jackson et al. | |
| 8,246,909 B2 | 8/2012 | Williams et al. | |
| 2001/0004081 A1 | 6/2001 | Tansley et al. | |
| 2007/0102044 A1 * | 5/2007 | Patzek, IV | A61B 1/123 137/212 |

* cited by examiner

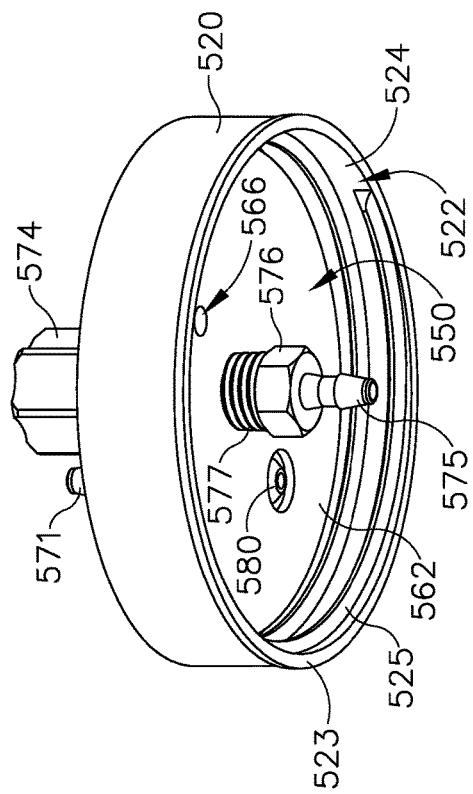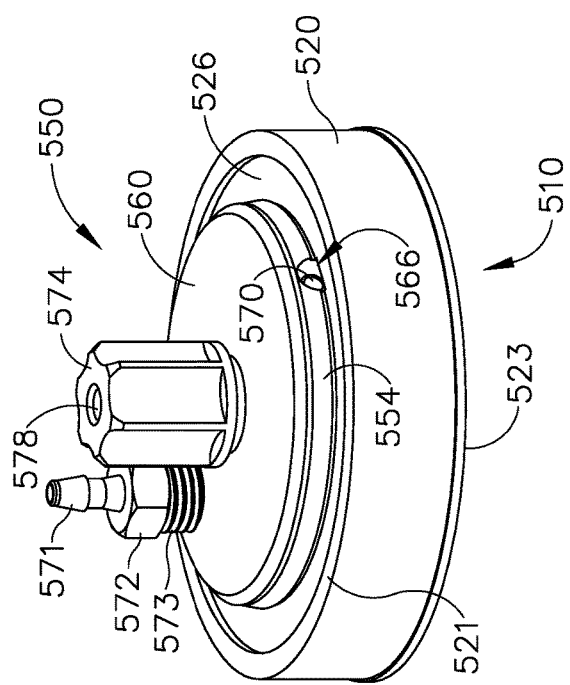

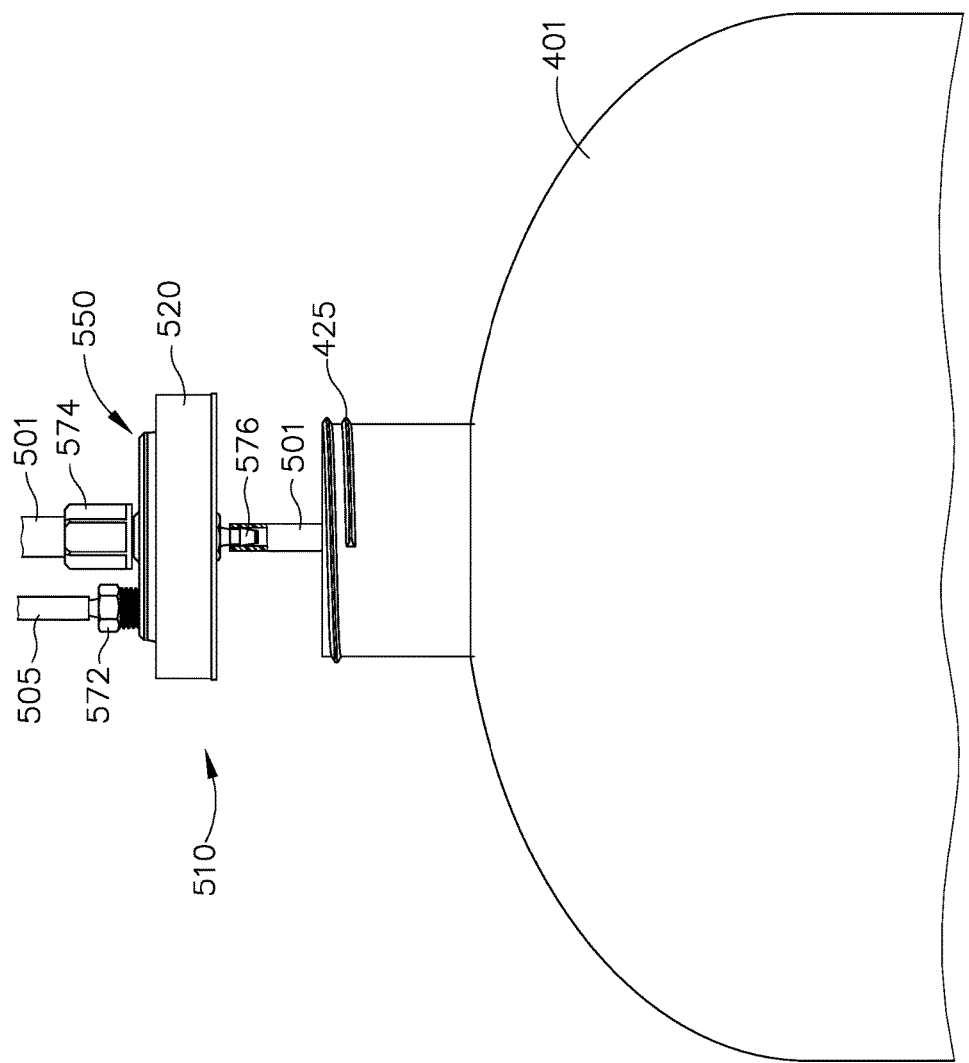

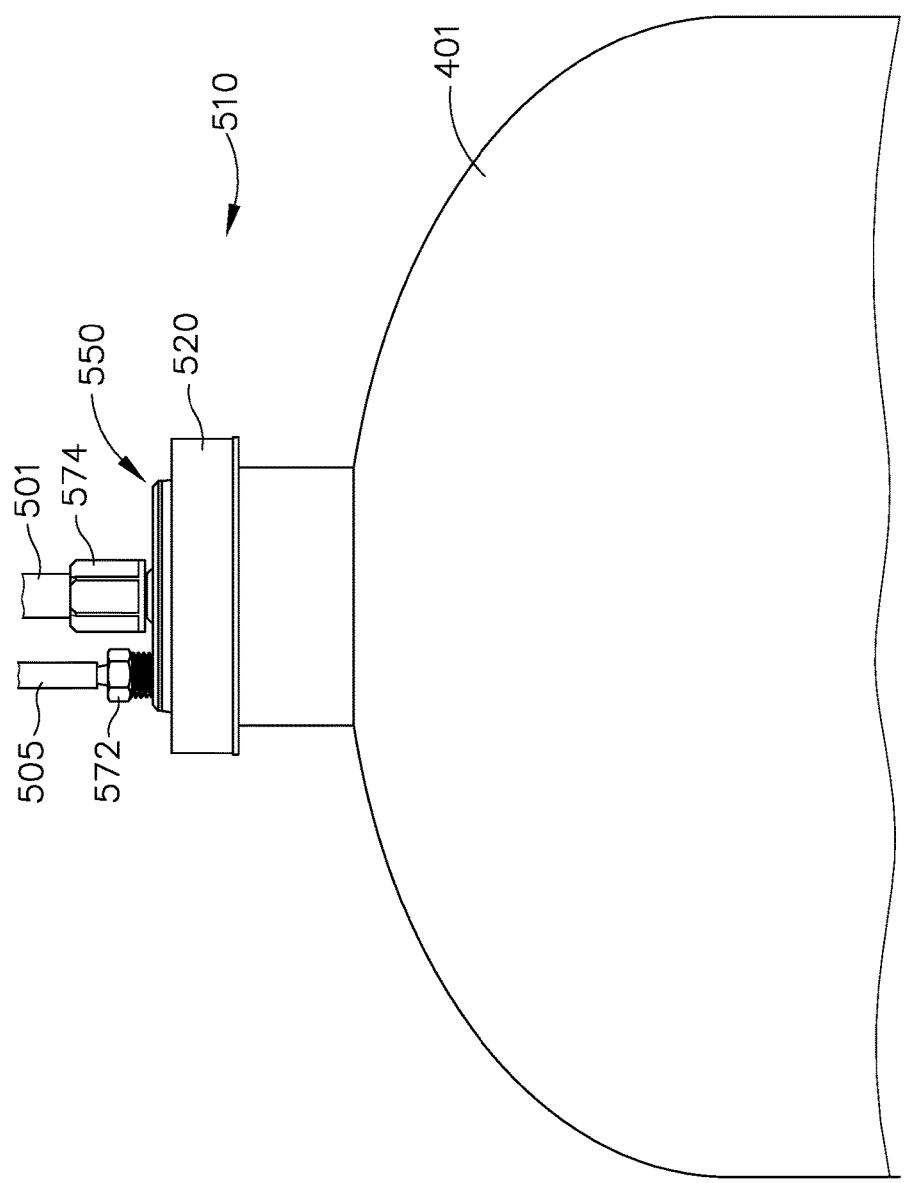

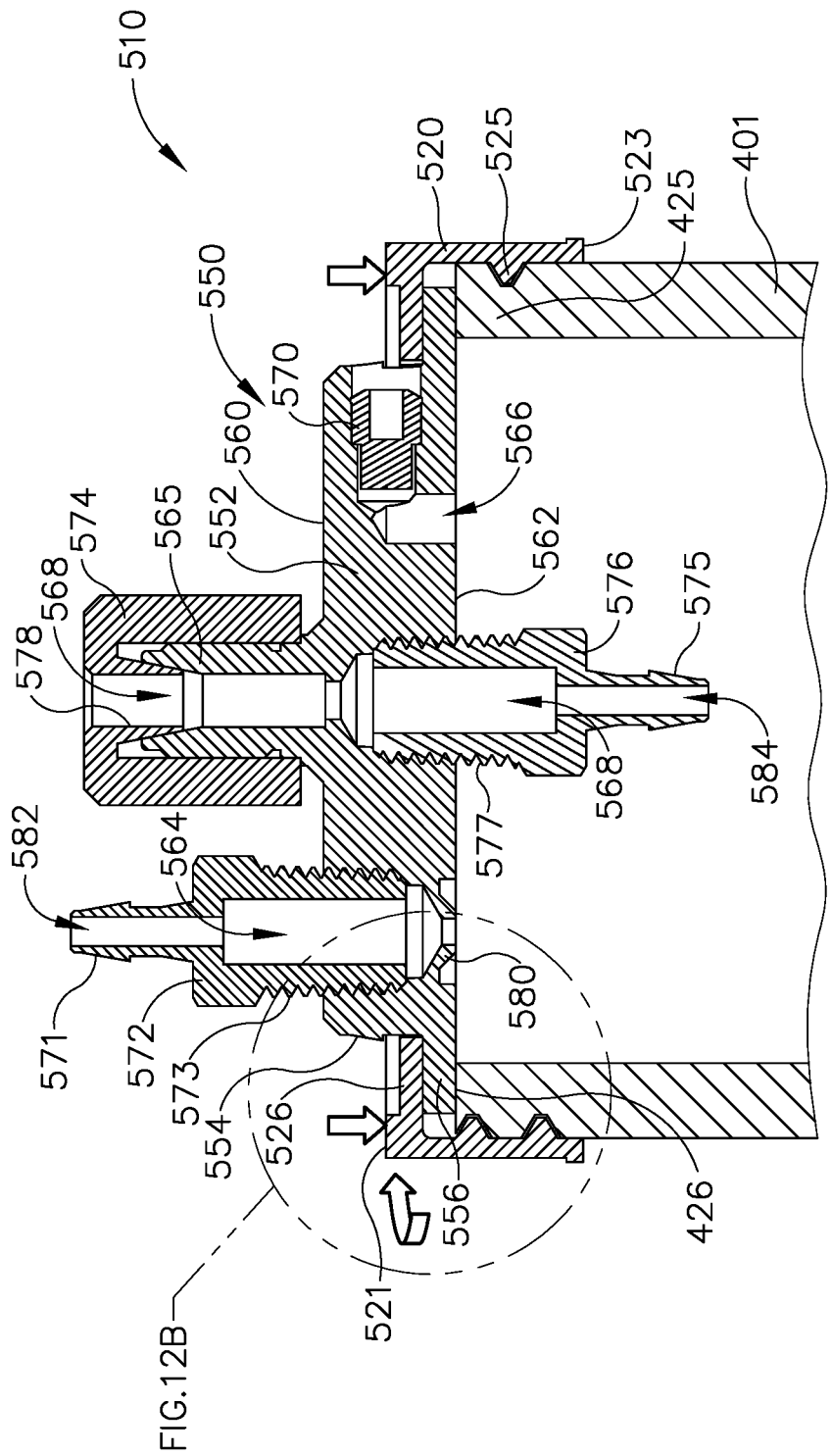

MULTI-PORT CAP FOR REAGENT CONTAINER

BACKGROUND

The below discussion relates to the reprocessing (i.e., decontamination) of endoscopes and other instruments that are used in medical procedures. In particular, the below discussion relates to an apparatus and a method that may be used to reprocess a medical device such as an endoscope after the medical device has been used in a first medical procedure, such that the medical device may be safely used in a subsequent medical procedure. While the below discussion will speak mainly in terms of an endoscope, it should be understood that the discussion may also equally apply to certain other medical devices.

An endoscope may have one or more working channels or lumens extending along at least a portion of the length of the endoscope. Such channels may be configured to provide a pathway for passage of other medical devices, etc., into an anatomical region within a patient. These channels may be difficult to clean and/or disinfect using certain primitive cleaning and/or disinfecting techniques. Thus, the endoscope may be placed in a reprocessing system that is particularly configured to clean endoscopes, including the channels within endoscopes. Such an endoscope reprocessing system may wash and disinfect the endoscope. Such an endoscope reprocessing system may include a basin that is configured to receive the endoscope, with a pump that flows cleaning fluids over the exterior of the endoscope within the basin. The system may also include ports that couple with the working channels of the endoscope and associated pumps that flow cleaning fluids through the working channels of the endoscope. The process executed by such a dedicated endoscope reprocessing system may include a detergent washing cycle, followed by a rinsing cycle, followed by a sterilization or disinfection cycle, followed by another rinsing cycle. The sterilization or disinfection cycle may employ disinfectant solution and water rinses. The process may optionally include an alcohol flush to aid displacement of water. A rinsing cycle may be followed by an air flush for drying and storage.

Examples of systems and methods that may be used to reprocess a used endoscope are described in U.S. Pat. No. 6,986,736, entitled "Automated Endoscope Reprocessor Connection with Integrity Testing," issued Jan. 17, 2006, the disclosure of which is incorporated by reference herein; U.S. Pat. No. 7,479,257, entitled "Automated Endoscope Reprocessor Solution Testing," issued Jan. 20, 2009, the disclosure of which is incorporated by reference herein; U.S. Pat. No. 7,686,761, entitled "Method of Detecting Proper Connection of an Endoscope to an Endoscope Reprocessor," issued Mar. 30, 2010, the disclosure of which is incorporated by reference herein; and U.S. Pat. No. 8,246,909, entitled "Automated Endoscope Reprocessor Germicide Concentration Monitoring System and Method," issued Aug. 21, 2012, the disclosure of which is incorporated by reference herein. An example of a commercially available endoscope reprocessing system is the EVOTECH® Endoscope Cleaner and Reprocessor (ECR) by Advanced Sterilization Products of Irvine, Calif.

Some versions of reprocessing systems may provide just a single use of a certain volume of disinfectant solution, such that the used volume of disinfectant solution is disposed of after a single use of the volume of disinfectant solution upon completion of the disinfection cycle. Some other versions of reprocessing system may check the concentration level of a used volume of disinfectant solution and either re-use the used disinfectant solution (i.e., if the concentration level is still acceptable) or dispose of the used disinfectant solution (i.e., if the concentration level is no longer acceptable). Examples of versions of reprocessing systems that provide monitoring and re-use of disinfectant solution are disclosed in U.S. Pat. No. 8,246,909, entitled "Automated Endoscope Reprocessor Germicide Concentration Monitoring System and Method," issued Aug. 21, 2012, the disclosure of which is incorporated by reference herein; in U.S. patent application Ser. No. 15/157,800, entitled "Apparatus and Method for Reprocessing a Medical Device," filed on May 18, 2016, the disclosure of which is incorporated by reference herein; and in in U.S. patent application Ser. No. 15/157,952, entitled "Apparatus and Method to Measure Concentration of Disinfectant in Medical Device Reprocessing system," filed on May 18, 2016, the disclosure of which is incorporated by reference herein.

While a variety of systems and methods have been made and used to reprocess medical devices, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 5 depicts a perspective view of an exemplary reservoir cap that may couple with a fluid reservoir of the disinfectant concentration measuring subsystem of FIG. 4;

FIG. 6 depicts another perspective view of the reservoir cap of FIG. 5;

FIG. 7A depicts a side elevational view of the reservoir cap of FIG. 5 placed above the fluid reservoir of the disinfectant concentration measuring subsystem of FIG. 4;

FIG. 7B depicts a side elevational view of the reservoir cap of FIG. 5 coupled with the fluid reservoir of the disinfectant concentration measuring subsystem of FIG. 4;

FIG. 11C depicts a cross-sectional view of the reservoir cap of FIG. 6 coupled with the fluid reservoir of the disinfectant concentration measuring subsystem of FIG. 4, where the rotating body of the reservoir cap is coupled with the fluid reservoir while also in contact with the static assembly of the reservoir cap;

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Medical Device Reprocessing Apparatus

Figure 1:
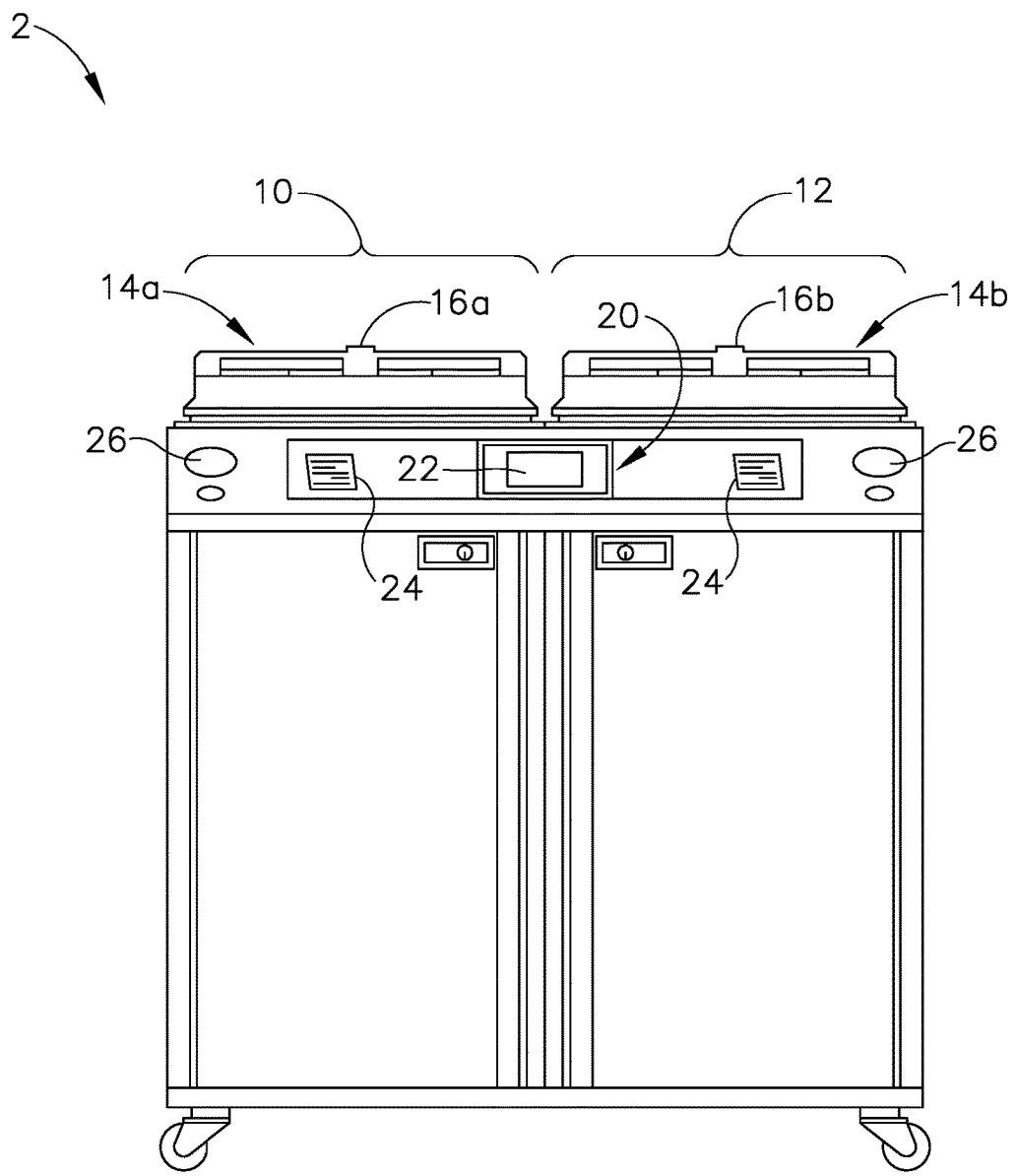
FIG. 1 depicts a front elevational view of an exemplary reprocessing system.
Figure 2:
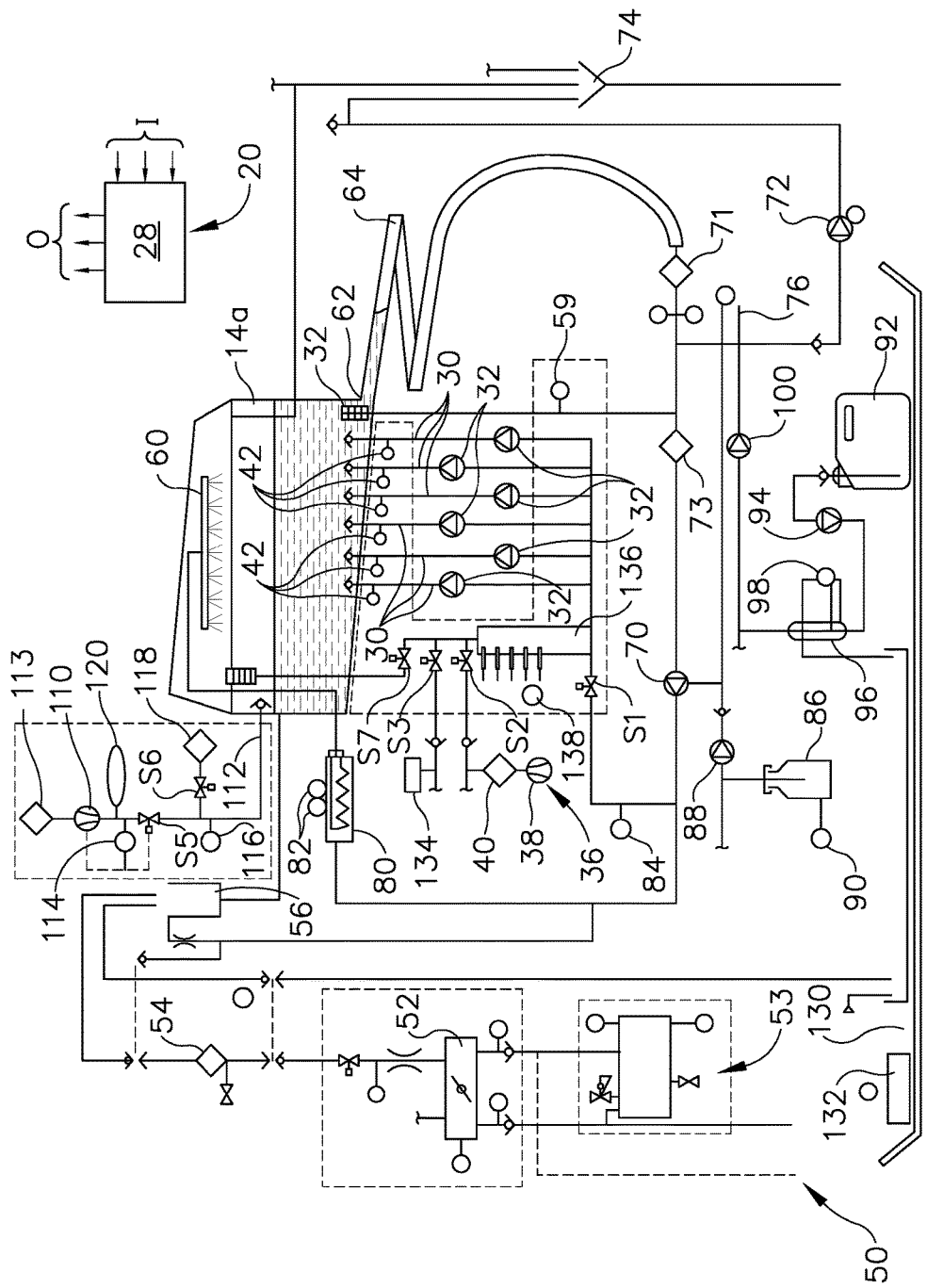
FIG. 2 depicts a schematic diagram of the reprocessing system of FIG. 1, with only a single decontamination basin shown for clarity.

FIGS. 1-2 show an exemplary reprocessing system (2) that may be used to decontaminate endoscopes and other medical devices that include channels or lumens formed therethrough. System (2) of this example generally includes a first station (10) and a second station (12). Stations (10, 12) are at least substantially similar in all respects to provide for the decontamination of two different medical devices simultaneously or in series. First and second decontamination basins (14a, 14b) receive the contaminated devices. Each basin (14a, 14b) is selectively sealed by a respective lid (16a, 16b). In the present example, lids (16a, 16b) cooperate with respective basins (14a, 14b) to provide a microbe-blocking relationship to prevent the entrance of environmental microbes into basins (14a, 14b) during decontamination operations. By way of example only, lids (16a, 16b) may include a microbe removal or HEPA air filter formed therein for venting.

A control system (20) includes one or more microcontrollers, such as a programmable logic controller (PLC), for controlling decontamination and user interface operations. Although one control system (20) is shown herein as controlling both decontamination stations (10, 12), those skilled in the art will recognize that each station (10, 12) can include a dedicated control system. A visual display (22) displays decontamination parameters and machine conditions for an operator, and at least one printer (24) prints a hard copy output of the decontamination parameters for a record to be filed or attached to the decontaminated device or its storage packaging. It should be understood that printer (24) is merely optional. In some versions, visual display (22) is combined with a touch screen input device. In addition, or in the alternative, a keypad and/or other user input feature is provided for input of decontamination process parameters and for machine control. Other visual gauges (26) such as pressure meters and the like provide digital or analog output of decontamination or medical device leak testing data.

FIG. 2 diagrammatically illustrates just one decontamination station (10) of reprocessing system (2), but those skilled in the art will recognize that decontamination station (12) may be configured and operable just like decontamination station (10). It should also be understood that reprocessing system (2) may be provided with just one single decontamination station (10, 12) or more than two decontamination stations (10, 12).

Decontamination basin (14a) receives an endoscope (200) (see FIG. 3) or other medical device therein for decontamination. Any internal channels of endoscope (200) are connected with flush conduits, such as flush lines (30). Each flush line (30) is connected to an outlet of a corresponding pump (32), such that each flush line (30) has a dedicated pump (32) in this example. Pumps (32) of the present example comprise peristaltic pumps that pump fluid, such as liquid and air, through the flush lines (30) and any internal channels of endoscope (200). Alternatively, any other suitable kind of pump(s) may be used. In the present example, pumps (32) can either draw liquid from basin (14a) through a filtered drain and a valve (S1); or draw decontaminated air from an air supply system (36) through a valve (S2). Air supply system (36) of the present example includes a pump (38) and a microbe removal air filter (40) that filters microbes from an incoming air stream.

A pressure switch or sensor (42) is in fluid communication with each flush line (30) for sensing excessive pressure in the flush line. Any excessive pressure or lack of flow sensed may be indicative of a partial or complete blockage (e.g., by bodily tissue or dried bodily fluids) in an endoscope (200) channel to which the relevant flush line (30) is connected. The isolation of each flush line (30) relative to the other flush lines (30) allows the particular blocked channel to be easily identified and isolated, depending upon which sensor (42) senses excessive pressure or lack of flow.

Basin (14a) is in fluid communication with a water source (50), such as a utility or tap water connection including hot and cold inlets, and a mixing valve (52) flowing into a break tank (56). A microbe removal filter (54), such as a 0.2 μm or smaller absolute pore size filter, decontaminates the incoming water, which is delivered into break tank (56) through the air gap to prevent backflow. A sensor (59) monitors liquid levels within basin (14a). An optional water heater (53) can be provided if an appropriate source of hot water is not available. The condition of filter (54) can be monitored by directly monitoring the flow rate of water therethrough or indirectly by monitoring the basin fill time using a float switch or the like. When the flow rate drops below a select threshold, this indicates a partially clogged filter element that requires replacement.

A basin drain (62) drains liquid from basin (14a) through an enlarged helical tube (64) into which elongated portions of endoscope (200) can be inserted. Drain (62) is in fluid communication with a recirculation pump (70) and a drain pump (72). Recirculation pump (70) recirculates liquid from basin drain (62) to a spray nozzle assembly (60), which sprays the liquid into basin (14a) and onto endoscope (200). A coarse screen (71) and a fine screen (73) filter out particles in the recirculating fluid. Drain pump (72) pumps liquid from basin drain (62) to a utility drain (74). A level sensor (76) monitors the flow of liquid from pump (72) to utility drain (74). Pumps (70, 72) can be simultaneously operated such that liquid is sprayed into basin (14a) while basin (14a) is being drained, to encourage the flow of residue out of basin (14a) and off of endoscope (200). Of course, a single pump and a valve assembly could replace dual pumps (70, 72).

An inline heater (80), with temperature sensors (82), upstream of recirculation pump (70), heats the liquid to optimum temperatures for cleaning and/or disinfection. A pressure switch or sensor (84) measures pressure downstream of circulation pump (70). In some variations, a flow sensor is used instead of pressure sensor (84), to measure fluid flow downstream of circulation pump (70). Detergent solution (86) is metered into the flow downstream of circulation pump (70) via a metering pump (88). A float switch (90) indicates the level of detergent (86) available. Disinfectant (92) is metered into the flow upstream of circulation pump (70) via a metering pump (94). To more accurately meter disinfectant (92), pump (94) fills a metering prechamber (96) under control of a fluid level switch (98) and control system (20). By way of example only, disinfectant solution (92) may comprise CIDEX© Activated Glutaraldehyde Solution by Advanced Sterilization Products of Irvine, Calif. By way of further example only, disinfectant solution (92) may comprise ortho-phthalaldehyde (OPA). By way of further example only, disinfectant solution (92) may comprise peracetic acid (PAA).

Some endoscopes (200) include a flexible outer housing or sheath surrounding the individual tubular members and the like that form the interior channels and other parts of endoscope (200). This housing defines a closed interior space, which is isolated from patient tissues and fluids during medical procedures. It may be important that the sheath be maintained intact, without cuts or other holes that would allow contamination of the interior space beneath the sheath. Therefore, reprocessing system (2) of the present example includes means for testing the integrity of such a sheath. In particular, an air pump (e.g., pump (38) or another pump (110)) pressurizes the interior space defined by the sheath of endoscope (200) through a conduit (112) and a valve (S5). In the present example, a HEPA or other microbe-removing filter (113) removes microbes from the pressurizing air. A pressure regulator (114) prevents accidental over pressurization of the sheath. Upon full pressurization, valve (S5) is closed and a pressure sensor (116) looks for a drop in pressure in conduit (112), which would indicate the escape of air through the sheath of endoscope (200). A valve (S6) selectively vents conduit (112) and the sheath of endoscope (200) through an optional filter (118) when the testing procedure is complete. An air buffer (120) smoothes out pulsation of pressure from air pump (110).

In the present example, each station (10, 12) also contains a drip basin (130) and spill sensor (132) to alert the operator to potential leaks.

An alcohol supply (134), controlled by a valve (S3), can supply alcohol to channel pumps (32) after rinsing steps, to assist in removing water from channels (210, 212, 213, 214, 217, 218) of endoscope (200).

Flow rates in lines (30) can be monitored via channel pumps (32) and pressure sensors (42). If one of pressure sensors (42) detects too high a pressure, the associated pump (32) is deactivated. The flow rate of pump (32) and its activated duration time provide a reasonable indication of the flow rate in an associated line (30). These flow rates are monitored during the process to check for blockages in any of the channels of endoscope (200). Alternatively, the decay in the pressure from the time pump (32) cycles off can also be used to estimate the flow rate, with faster decay rates being associated with higher flow rates.

A more accurate measurement of flow rate in an individual channel may be desirable to detect subtler blockages. To that end, a metering tube (136) having a plurality of level indicating sensors (138) fluidly connects to the inputs of channel pumps (32). In some versions, a reference connection is provided at a low point in metering tube (136) and a plurality of sensors (138) are arranged vertically above the reference connection. By passing a current from the reference point through the fluid to sensors (138), it can be determined which sensors (138) are immersed and therefore determine the level within metering tube (136). In addition, or in the alternative, any other suitable components and techniques may be used to sense fluid levels. By shutting valve (S1) and opening a vent valve (S7), channel pumps (32) draw exclusively from metering tube (136). The amount of fluid being drawn can be very accurately determined based upon sensors (138). By running each channel pump (32) in isolation, the flow therethrough can be accurately determined based upon the time and the volume of fluid emptied from metering tube (136).

In addition to the input and output devices described above, all of the electrical and electromechanical devices shown are operatively connected to and controlled by control system (20). Specifically, and without limitation, switches and sensors (42, 59, 76, 84, 90, 98, 114, 116, 132 136) provide input (I) to microcontroller (28), which controls the cleaning and/or disinfection cycles and other machine operations in accordance therewith. For example, microcontroller (28) includes outputs (0) that are operatively connected to pumps (32, 38, 70, 72, 88, 94, 100, 110), valves (S1, S2, S3, S5, S6, S7), and heater (80) to control these devices for effective cleaning and/or disinfection cycles and other operations.

Figure 3:
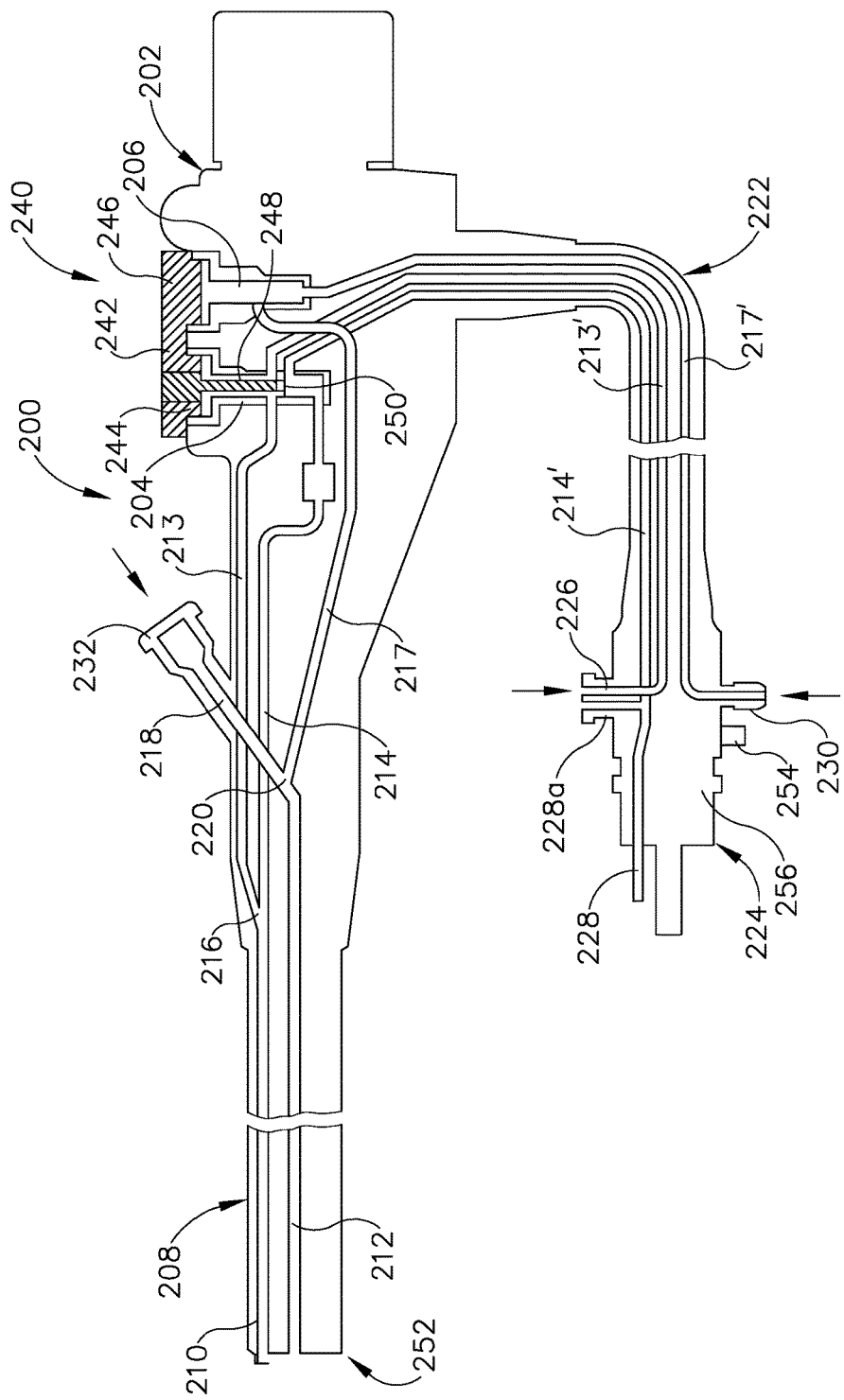
FIG. 3 depicts a cross-sectional side view of proximal and distal portions of an endoscope that may be decontaminated using the reprocessing system of FIG. 1.

As shown in FIG. 3, endoscope (200) has a head part (202). Head part (202) includes openings (204, 206) formed therein. During normal use of endoscope (200), an air/water valve (not shown) and a suction valve (not shown) are arranged in openings (204, 206). A flexible shaft (208) is attached to head part (202). A combined air/water channel (210) and a combined suction/biopsy channel (212) are accommodated in shaft (208). A separate air channel (213) and water channel (214) are also arranged in head part (202) and merge into air/water channel (210) at the location of a joining point (216). It will be appreciated that the term "joining point" as used herein refers to an intersecting junction rather than being limited to a geometrical point and, the terms may be used interchangeably. Furthermore, a separate suction channel (217) and biopsy channel (218) are accommodated in head part (202) and merge into suction/biopsy channel (212) at the location of a joining point (220).

In head part (202), air channel (213) and water channel (214) open into opening (204) for the air/water valve (not shown). Suction channel (217) opens into opening (206) for the suction valve (not shown). Furthermore, a flexible feed hose (222) connects to head part (202) and accommodates channels (213', 214', 217'), which are connected to air channel (213), water channel (214), and suction channel (217) via respective openings (204, 206). In practice, feed hose (222) may also be referred to as the light-conductor casing. The mutually connecting air channels (213, 213') will collectively be referred to below as air channel (213). The mutually connecting water channels (214, 214') will collectively be referred to below as water channel (214). The mutually connecting suction channels (217, 217') will collectively be referred to below as suction channel (217). A connection (226) for air channel (213), connections (228, 228a) for water channel (214), and a connection (230) for suction channel (217) are arranged on the end section (224) (also referred to as the light conductor connector) of flexible hose (222). When the connection (226) is in use, connection (228a) is closed off. A connection (232) for biopsy channel (218) is arranged on head part (202).

A channel separator (240) is shown inserted into openings (204, 206). Channel separator (240) comprises a body (242) and plug members (244, 246), which occlude respective openings (204, 206). A coaxial insert (248) on plug member (244) extends inwardly of opening (204) and terminates in an annular flange (250), which occludes a portion of opening (204) to separate channel (213) from channel (214). By connecting lines (30) to openings (226, 228, 228a, 230, 232), liquid for cleaning and disinfection can be flowed through endoscope channels (213, 214, 217, 218) and out of a distal tip (252) of endoscope (200) via channels (210, 212). Channel separator (240) ensures that such liquid flows all the way through endoscope (200) without leaking out of openings (204, 206); and isolates channels (213, 214) from each other so that each channel (213, 214) has its own independent flow path. One of skill in the art will appreciate that various endoscopes having differing arrangements of channels and openings may require modifications to channel separator (240) to accommodate such differences while occluding ports in head (202) and keeping channels separated from each other so that each channel can be flushed independently of the other channels. Otherwise, a blockage in one channel might merely redirect flow to a connected unblocked channel.

A leakage port (254) on end section (224) leads into an interior portion (256) of endoscope (200) and is used to check for the physical integrity thereof, namely to ensure that no leakage has formed between any of the channels and the interior (256) or from the exterior to the interior (256).

II. Exemplary Medical Device Reprocessing Method

In an exemplary use of reprocessing system (2), an operator may start by actuating a foot pedal (not shown) to open basin lid (16a). Each lid (16a, 16b) may have its own foot pedal. In some versions, once pressure is removed from the foot pedal, the motion of lid (16a, 16b) stops. With lid (16a) open, the operator inserts shaft (208) of endoscope (200) into helical circulation tube (64). End section (224) and head section (202) of endoscope (200) are situated within basin (14a), with feed hose (222) coiled within basin (14a) with as wide a diameter as possible. Next, flush lines (30) are attached to respective endoscope openings (226, 228, 228a, 230, 232). Air line (112) is also connected to connector (254). In some versions, flush lines (30) are color coded, and guide located on station (10) provides a reference for the color-coded connections.

Depending on the customer-selectable configuration, control system (20) may prompt the operator to enter a user code, patient ID, endoscope code, and/or specialist code. This information may be entered manually (e.g., through touch screen (22)), automatically (e.g., by using an attached barcode wand), or in any other suitable fashion. With the information entered (if required), the operator may then close lid (16a). In some versions, closing lid (16a) requires the operator to press a hardware button and a touch-screen (22) button simultaneously to provide a fail-safe mechanism for preventing the operator's hands from being caught or pinched by the closing basin lid (16a). If either the hardware button or software button is released while lid (16a) is in the process of closing, the motion of lid (16a) stops.

Once lid (16a) is closed, the operator presses a button on touch-screen (22) to begin the washing/disinfection process. At the start of the washing/disinfection process, air pump (38) is activated and pressure within the body of endoscope (200) is monitored. When pressure reaches a predetermined level (e.g., 250 mbar), pump (38) is deactivated, and the pressure is allowed to stabilize for a certain stabilization period (e.g., 6 seconds). If pressure has not reached a certain pressure (e.g., 250 mbar) in a certain time period (e.g., 45 seconds), the program is stopped and the operator is notified of a leak. If pressure drops below a threshold (e.g., less than 100 mbar) during the stabilization period, the program is stopped and the operator is notified of the condition. Once the pressure has stabilized, the pressure drop is monitored over the course of a certain duration (e.g., 60 seconds). If pressure drop is faster than a predetermined rate (e.g., more than 10 mbar within 60 seconds), the program is stopped and the operator is notified of the condition. If the pressure drop is slower than a predetermined rate (e.g., less than 10 mbar in 60 seconds), reprocessing system (2) continues with the next step. A slight positive pressure is held within the body of endoscope (200) during the rest of the process to prevent fluids from leaking in.

A second leak test checks the adequacy of connection to the various ports (226, 228, 228a, 230, 232) and the proper placement of channel separator (240). A quantity of water is admitted to basin (14a) so as to submerge the distal end of endoscope (200) in helical tube (64). Valve (S1) is closed and valve (S7) opened; and pumps (32) are run in reverse to draw a vacuum and to ultimately draw liquid into endoscope channels (210, 212). Pressure sensors (42) are monitored to make sure that the pressure in any one channel (210, 212) does not drop and/or raise by more than a predetermined amount in a given time frame. If it does, it likely indicates that one of the connections was not made correctly and air is leaking into channel (210, 212). In any event, in the presence of an unacceptable pressure drop, control system (20) will cancel the cycle and indicate a likely faulty connection, preferably with an indication of which channel (210, 212) failed.

In the event that the leak tests are passed, reprocessing system (2) continues with a pre-rinse cycle. The purpose of this step is to flush water through channels (210, 212, 213, 214, 217, 218) to remove waste material prior to washing and disinfecting endoscope (200). To initiate the pre-rinse cycle, basin (14a) is filled with filtered water and the water level is detected by pressure sensor (59) below basin (14a). The water is pumped via pumps (32) through the interior of channels (210, 212, 213, 214, 217, 218), directly to drain (74). This water is not recirculated around the exterior surfaces of endoscope 200 during this stage. As the water is being pumped through channels (210, 212, 213, 214, 217, 218), drain pump (72) is activated to ensure that basin (14a) is also emptied. Drain pump (72) will be turned off when drain switch (76) detects that the drain process is complete. During the draining process, sterile air is blown via air pump (38) through all endoscope channels (210, 212, 213, 214, 217, 218) simultaneously, to minimize potential carryover.

Once the pre-rinse cycle is complete, reprocessing system (2) continues with a wash cycle. To begin the wash cycle, basin (14a) is filled with warm water (e.g., approximately 35° C.). Water temperature is controlled by controlling the mix of heated and unheated water. The water level is detected by pressure sensor (59). Reprocessing system (2) then adds enzymatic detergent to the water circulating in reprocessing system (2) by means of peristaltic metering pump (88). The volume is controlled by controlling the delivery time, pump speed, and inner diameter of the tubing of pump (88). Detergent solution (86) is actively pumped throughout the internal endoscope channels (210, 212, 213, 214, 217, 218) and over the outer surface of endoscope (200) for a predetermined time period (e.g., from one to five minutes, or more particularly about three minutes), by channel pumps (32) and external circulation pump (70). Inline heater (80) keeps the temperature at a predetermined temperature (e.g., approximately about 35° C.).

After detergent solution (86) has been circulating for a certain period of time (e.g., a couple of minutes), the flow rate through channels (210, 212, 213, 214, 217, 218) is measured. If the flow rate through any channel (210, 212, 213, 214, 217, 218) is less than a predetermined rate for that channel (210, 212, 213, 214, 217, 218), the channel (210, 212, 213, 214, 217, 218) is identified as blocked, the program is stopped, and the operator is notified of the condition. Peristaltic pumps (32) are run at their predetermined flow rates and cycle off in the presence of unacceptably high pressure readings at the associated pressure sensor (42). If a channel (210, 212, 213, 214, 217, 218) is blocked, the predetermined flow rate will trigger pressure sensor (42), indicating the inability to adequately pass this flow rate. As pumps (32) are peristaltic in the present example, their operating flow rate combined with the percentage of time they are cycled off due to pressure will provide the actual flow rate. The flow rate can also be estimated based upon the decay of the pressure from the time pump (32) cycles off.

At the end of the wash cycle, drain pump (72) is activated to remove detergent solution (86) from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover.

After the wash cycle is complete, reprocessing system (2) begins a rinse cycle. To initiate this rinse cycle, basin (14a) is again filled with warm water (e.g., at approximately 35° C.). Water temperature is controlled by controlling the mix of heated and unheated water. The water level is detected by pressure sensor (59). The rinse water is circulated within channels (210, 212, 213, 214, 217, 218) of endoscope (200) via channel pumps (32); and over the exterior of endoscope (200) via circulation pump (70) and sprinkler arm (60) for a certain period of time (e.g., one minute). As rinse water is pumped through channels (210, 212, 213, 214, 217, 218), the flow rate through channels (210, 212, 213, 214, 217, 218) is measured and if it falls below the predetermined rate for any given channel (210, 212, 213, 214, 217, 218), that channel (210, 212, 213, 214, 217, 218) is identified as blocked, the program is stopped, and the operator is notified of the condition.

At the end of the rinse cycle, drain pump (72) is activated to remove the rinse water from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover. In some versions, the above-described rinsing and draining cycles are repeated at least once again, to ensure maximum rinsing of detergent solution (86) from the surfaces of endoscope (200) and basin (14a).

After reprocessing system (2) has completed the desired number of rinsing and drying cycles, reprocessing system (2) proceeds to a disinfection cycle. To initiate the disinfection cycle, basin (14a) is filled with very warm water (e.g., at approximately 53° C.). Water temperature is controlled by controlling the mix of heated and unheated water. The water level is detected by pressure sensor (59). During the filling process, channel pumps (32) are off in order to ensure that the disinfectant solution (92) in basin (14a) is at the in-use concentration prior to circulating through channels (210, 212, 213, 214, 217, 218) of endoscope (200).

Next, a measured volume of disinfectant solution (92) is drawn from disinfectant metering pre-chamber (96) and delivered into the water in basin (14a) via metering pump (100). The volume of disinfectant solution (92) is controlled by the positioning of fill level switch (98) relative to the bottom of metering pre-chamber (96). Metering pre-chamber (96) is filled until fill level switch (98) detects liquid. Disinfectant solution (92) is drawn from metering pre-chamber (96) until the level of disinfectant solution (92) in metering pre-chamber (96) is just below the tip of metering pre-chamber (96). After the necessary volume is dispensed, metering pre-chamber (96) is refilled from the bottle of disinfectant solution (92). Disinfectant solution (92) is not added until basin (14a) is filled, so that in case of a water supply problem, concentrated disinfectant is not left on endoscope (200) with no water to rinse it. While disinfectant solution (92) is being added, channel pumps (32) are off in order to ensure that disinfectant solution (92) in basin (14a) is at the desired in-use concentration prior to circulating through channels (210, 212, 213, 214, 217, 218) of endoscope (200).

The in-use disinfectant solution (92) is actively pumped throughout internal channels (210, 212, 213, 214, 217, 218) by pumps (32) and over the outer surface of endoscope (200) by circulation pump (70). This may be done for any suitable duration (e.g., at least 5 minutes). The temperature of the disinfectant solution (92) may be controlled by in-line heater (80) to stay at a consistent temperature (e.g., about 52.5° C.). During the disinfection process, flow through each channel (210, 212, 213, 214, 217, 218) of endoscope (200) is verified by timing the delivering a measured quantity of solution through channel (210, 212, 213, 214, 217, 218). Valve (S1) is closed, and valve (S7) opened, and in turn each channel pump (32) delivers a predetermined volume to its associated channel (210, 212, 213, 214, 217, 218) from metering tube (136). This volume and the time it takes to deliver the volume, provides a very accurate flow rate through the channel (210, 212, 213, 214, 217, 218). Anomalies in the flow rate from what is expected for a channel (210, 212, 213, 214, 217, 218) of that diameter and length are flagged by control system (20) and the process stopped. As in-use disinfectant solution (92) is pumped through channels (210, 212, 213, 214, 217, 218), the flow rate through channels (210, 212, 213, 214, 217, 218) is also measured as described above.

At the end of the disinfection cycle, drain pump (72) is activated to remove disinfectant solution (92) solution from basin (14a) and channels (210, 212, 213, 214, 217, 218). During the draining process, sterile air is blown through all channels (210, 212, 213, 214, 217, 218) of endoscope (200) simultaneously to minimize potential carryover. As will be described in greater detail below, in some versions, the used disinfectant solution (92) is tested to determine whether the concentration level is within an acceptable range or if the used disinfectant solution (92) has been diluted to a point where the used disinfectant solution (92) is below a certain concentration threshold. If the used disinfectant solution (92) has acceptable concentration level, the used disinfectant solution (92) may be used again in subsequent disinfection cycles. If the used disinfectant solution (92) has a concentration below the threshold, the used disinfectant solution (92) may be disposed of (e.g., via drain (74)).

After disinfectant solution (92) has been drained from basin (14a), reprocessing system (2) begins a final rinse cycle. To initiate this cycle, basin (14a) is filled with sterile warm water (e.g., at approximately 45° C.) that has been passed through a filter (e.g., a 0.2 μm filter). The rinse water is circulated within channels (210, 212, 213, 214, 217, 218) by pumps (32); and over the exterior of endoscope (200) via circulation pump (70) and sprinkler arm 60) for a suitable duration (e.g., 1 minute). As rinse water is pumped through channels (210, 212, 213, 214, 217, 218), the flow rate through channels (210, 212, 213, 214, 217, 218) is measured as described above. Drain pump (72) is activated to remove the rinse water from basin (14a) and channels (210, 212, 213, 214, 217, 218). During the draining process, sterile air is blown through all channels (210, 212, 213, 214, 217, 218) of endoscope (200) simultaneously to minimize potential carryover. In some versions, the above-described rinsing and draining cycles are repeated at least two more times, to ensure maximum rinsing of disinfectant solution (92) residuals from the surfaces of endoscope (200) and basin (14a).

After the final rinse cycle is complete, reprocessing system (2) begins a final leak test. In particular, reprocessing system (2) pressurizes the body of endoscope (200) and measures the leak rate as described above. If the final leak test is successful, reprocessing system (2) indicates the successful completion of the cycles via touch-screen (22). From the time of program completion to the time at which lid (16a) is opened, pressure within the body of endoscope (200) is normalized to atmospheric pressure by opening vent valve (S5) at a predetermined rate (e.g., valve (S5) opened for 10 seconds every minute).

Depending on customer-selected configuration, reprocessing system (2) may prevent lid (16a) from being opened until a valid user identification code is entered. Information about the completed program, including the user ID, endoscope ID, specialist ID, and patient ID are stored along with the sensor data obtained throughout the program. If a printer is connected to reprocessing system (2), and if requested by the operator, a record of the disinfection program will be printed. Once a valid user identification code has been entered, lid (16a) may be opened (e.g., using the foot pedal as described above). Endoscope (200) is then disconnected from flush lines (30) and removed from basin (14a). Lid (16a) can then be closed using both the hardware and software buttons as described above.

III. Exemplary Disinfectant Concentration Measuring Subsystem

As noted above, some versions of reprocessing system (2) use a certain volume of disinfectant solution (92) only once, such that the volume of disinfectant solution (92) is disposed of at the end of a disinfection cycle; while other versions of reprocessing system (2) provide re-use of the same volume of disinfectant solution (92) in two or more disinfection cycles. In versions that provide re-use of disinfectant solution (92) in two or more disinfection cycles, it may be desirable to measure the concentration of disinfectant in disinfectant solution (92) after each use, to ensure that disinfectant solution (92) is still at a concentration level that is high enough to provide effective disinfection of medical devices.

Figure 4:
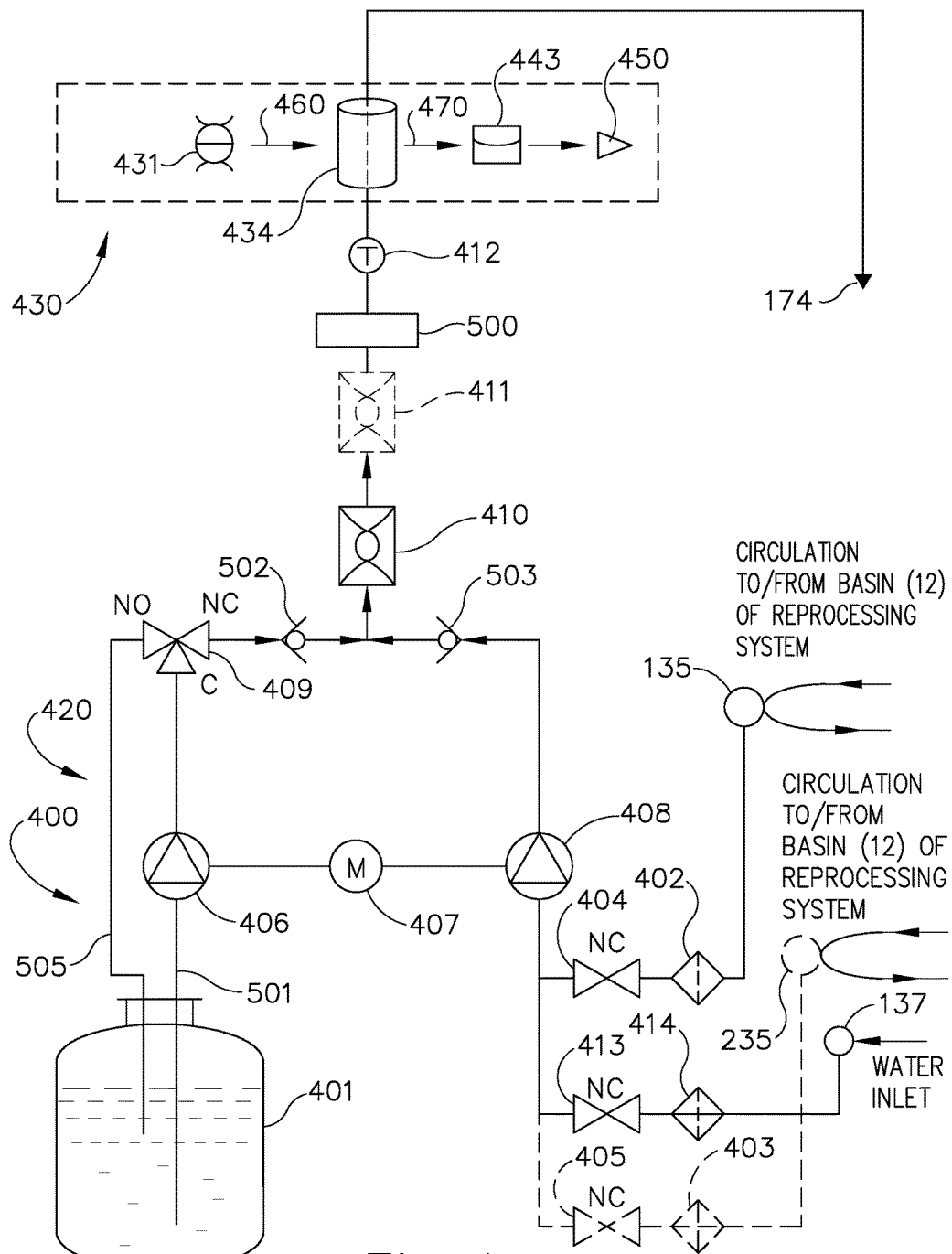
FIG. 4 is a diagrammatic illustration of a disinfectant concentration measuring subsystem that may be incorporated into the reprocessing system of FIG. 1.

FIG. 4 shows a diagrammatic illustration of an exemplary disinfectant concentration measuring subsystem (400), hereinafter, "subsystem (400)." Subsystem (400) measures disinfectant concentration of disinfectant solution (92) that is used, and often re-circulated and re-used, in reprocessing system (2). Although subsystem (400) of this example may be used to measure disinfectant concentration of disinfectant solution (92) in reprocessing system (2) comprising either one station (10) or optionally, two stations (10, 12), it is contemplated herein that subsystem (400) may be readily adapted by one skilled in the art to sample disinfectant solution (92) from a reprocessing system comprising three or more stations. Subsystem (400) may be combined with reprocessing system (2) in a number of ways. For example, subsystem (400) may be fully integrated into reprocessing system (2). In a further example, subsystem (400) may be provided as a separate stand-alone unit that is placed in fluid communication with reprocessing system (2) (e.g., by coupling subsystem (400) with reprocessing system (2) via a fluid conduit, etc.).

It should also be understood that subsystem (400) may be incorporated into reprocessing system (2) in accordance with the teachings of U.S. Pat. No. 8,246,909 and/or the teachings of U.S. patent application Ser. No. 15/157,800, the disclosure of which is incorporated by reference herein, and/or U.S. patent application Ser. No. 15/157,952, the disclosure of which is incorporated by reference herein. Various other suitable ways in which subsystem (400) may be combined with reprocessing system (2) will be apparent to those of ordinary skill in the art in view of the teachings herein.

FIG. 4 shows a functional diagram of exemplary fluidics system (420) of subsystem (400). Fluidics system (420) may be configured for batch processing or continuous processing of disinfectant solution (92). Fluidics system (420) is connected to a first outlet (135) of reprocessing system (2). First outlet (135) provides circulation with first station (10). Fluidics system (420) is also connected to a second outlet (235) of reprocessing system (2). Second outlet (235) provides circulation with second station (12). It should be understood that, since second station (12) is merely optional, second outlet (235) is also merely optional.

First outlet (135) is also in fluid communication with first filter (402). First filter (402) is in fluid communication with first valve (404), which is normally in a closed state. If present, second outlet (235) is likewise in fluid communication with second filter (403). Second filter (403) is in fluid communication with second valve (405), which is normally in a closed state. Normally closed first valve (404) is opened when disinfectant solution (92) is to be sampled from first station (10), and alternatively, normally closed second valve (405) is opened when disinfectant solution (92) is to be sampled from second station (12). In any case, when first and/or second valves (404, 405) are closed, and motor ((407)

discussed below) stopped, subsystem (400) is in holding mode, and disinfectant solution (92) is free to circulate to and from reprocessing system (2). In order for continuous sampling of disinfectant solution (92) to occur, either first valve (404) or optional second valve (405) remains in an open state.

Fluidics system (420) of the present example is also in fluid communication with reservoir (401) that is configured to contain reagent solution. Reservoir (401) is in fluid communication with first pump (406), whereas aforementioned first valve (404) and optional second valve (405) are in fluid communication with second pump (408). In some versions such as the one shown in FIG. 4, first pump (406) and second pump (408) are simultaneously driven by dual-head stepper motor (407). Utilizing dual-head stepper motor (407) allows for precise and accurate control of volumetric flow of reagent solution and disinfectant solution (92) through respective pumps (406, 408). For example, disinfectant solution (92) and reagent solution may be simultaneously pumped at volumetric flow rate ratio of about 1:1. Alternatively, some other kind of motor and/or pumping arrangement may be used to pump at volumetric flow rate ratio of about 1:1 or any other desired volumetric flow rate ratio. Moreover, motor and/or pumping arrangements may be configured to change the volumetric flow rate ratio in real time, such as for example, by driving two pumps via two different motors to respectively pump the disinfectant solution (92) and the reagent solution.

In the example shown in FIG. 4, first pump (406) is in fluid communication with selector valve (409), which is in fluid communication with first mixing chamber (410). Selector valve (409) controls flow of reagent solution either back to reservoir (401) or to first mixing chamber (410). In the present example, when selector valve (409) is in the normally open state, reagent solution flows from reservoir (401), through first pump (406) and back into reservoir (401), which may allow for reagent supply line (501) to be purged and de-gassed without wasting reagent solution. Various suitable devices and methods that may be used to purge and/or de-gas reagent supply line (501) will be apparent to those of ordinary skill in the art in view of the teachings herein. It should also be understood that such purging and de-gassing features are merely optional. Some versions may simply omit such purging and de-gassing features.

When disinfectant solution (92) is to be measured for disinfectant concentration, the normally open portion of selector valve (409) closes and the normally closed portion of selector valve (409) opens to allow reagent solution to flow from reservoir (401), through first pump (406), through first check valve (502) and into first mixing chamber (410). First check valve (502) prevents flow back of fluid from first mixing chamber (410) back through selector valve (409) and ultimately back into reservoir (401) where the fluid may contaminate the reagent. In order for continuous sampling of disinfectant solution (92) to occur, selector valve (409) may remain in this position to continuously deliver reagent solution to first mixing chamber (410).

In fluidics system (420) of the present example, second pump (408) is also in fluid communication with first mixing chamber (410). Thus, when either first valve (404) or alternatively, optional second valve (405) is in an open state, disinfectant solution (92) is pumped through second check valve (503) and into first mixture chamber (410). Second check valve (503) prevents flow back of fluid from first mixing chamber (410) back into second pump (408). As noted above, in the present example shown in FIG. 4, first pump (406) and second pump (408) are simultaneously driven by dual-head stepper motor (407), which allows for precise and accurate control of volumetric flow of reagent solution and disinfectant solution (92) respectively through pumps (406, 408). Thus, volumes of reagent solution and disinfectant solution (92) delivered into first mixing chamber (410) may be precisely controlled and consequently, may be mixed in any desired ratio within first mixing chamber (410) to create sample solution. In some versions, reagent solution and disinfectant solution (92) may be mixed in a volume to volume ratio of about 1:1 to create sample solution.

As shown in FIG. 4, fluidics system (420) is also connected to water inlet (137). Water inlet (137) is in fluid communication with third filter (414). Third filter (414) is in fluid communication with third valve (413), which is normally in a closed position. Normally closed third valve (413) is opened when a baseline concentration of reagent product is to be determined. When third valve (413) is open, a volume of water (instead of a volume of disinfectant solution (92)) is mixed in the first mixing chamber (410) with a volume of reagent solution to create a blank solution. In some versions, reagent solution and water may be mixed in a volume to volume ratio of about 1:1 to create the blank solution. Absorbance of the blank solution is measured, as described below, and utilized by controller (050) to calculate absorbance of reaction product(s) of interest.

As shown in FIG. 4, first mixing chamber (410) may optionally be in fluid communication with second mixing chamber (411). It is contemplated herein that more than two mixing chambers (410, 411) may be utilized. By way of example only, mixing chambers (410, 411) may each comprise a static mixer with a plurality of mixing elements. Various suitable forms that mixing chambers (410, 411) may take will be apparent to those of ordinary skill in the art in view of the teachings herein. One skilled in the art may chose the number of mixing chambers to include in subsystem (400) based upon a number of factors including, but not limited to, sample mixing time needed to generate reaction product having concentration in sample solution (or blank solution) that is measurable utilizing concentration analysis assembly (430) of subsystem (400). In any case, one or more of mixing chamber(s) (410, 411) are in fluid communication with de-gassing module (500). De-gassing module (500) is operable to remove air bubbles from the liquid solution passing through mixing chamber(s) (410, 411). Degassing module (500) is in fluid communication with sample chamber (434). It should be understood that degassing module (500) is merely optional. In some versions, degassing module (500) is omitted entirely.

Depending upon the chemical reaction that is desired when the reagent solution is mixed with the disinfectant solution (92), the temperature of the resulting sample solution may impact the absorbance measurement of the reaction product in the sample solution. Thus, in some versions, such as the one shown in FIG. 4, subsystem (400) includes temperature sensor (412), which is positioned such that it may measure the temperature of sample solution as the sample solution passes from mixing chamber (410, 411) into sample chamber (434). Temperature sensor (412) measures the temperature of sample solution to allow for temperature corrections by a controller (not shown) when determining disinfectant concentration in disinfectant solution (92). It should be understood that temperature sensor (412) is merely optional. In some versions, temperature sensor (412) is omitted entirely.

Concentration analysis assembly (430) of subsystem (400) is generally shown to comprise light emitting diode (431) and a photodiode sensor (443). Light emitting diode (431) is configured to emit light of first known intensity (460) and wavelength and to direct light through sample chamber (434). Sensor (443) measures a portion of light that passes through cuvette (434) and which has second intensity (470). The difference between known first light intensity (460) and second light intensity (470) is indicative of reaction product concentration in sample solution or blank solution. Controller (450) is configured to determine the concentration of reaction product in sample solution based upon sensed light data from sensor (443) in accordance with the Beer-Lambert law. Based upon the concentration of reaction product in sample solution, controller (450) is configured to determine the concentration of disinfectant in disinfectant solution (92).

A thermistor (not shown) may be configured to measure temperature of cuvette (434). Controller (450) may be configured to adjust the determination of disinfectant concentration due to any thermal impact on light measurements, as detected by thermistor (412).

As shown in FIG. 4, if the sample solution is no longer of use, the sample solution is outputted from concentration analysis assembly (430) of subsystem (400) via fluid output (174). Fluid output (174) may be coupled with one or more drains, for example, utility drain (74) of reprocessing system (2).

It should be understood from the foregoing that, if subsystem (400) determines that the concentration level of disinfectant solution (92) is above an appropriate threshold, subsystem (400) provides recirculation and re-use of disinfectant solution (92) in subsequent disinfection cycles performed by reprocessing system (2). However, subsystem (400) determines that the concentration level of disinfectant solution (92) is below an appropriate threshold, indicating that disinfectant solution (92) has become too diluted to continue being effective, subsystem (400) disposes of the diluted disinfectant solution (92). Reprocessing system (2) may then use additional, fresh disinfectant solution (92) in order to provide an effective concentration level.

IV. Exemplary Reservoir Cap

It may be desirable to place a cap on the opening of reservoir (401), with the cap being designed to couple reservoir (401) with both reagent supply line (501) and reagent return line (505). A cap may help prevent unwanted escape of reagent solution from the interior of reservoir (401) while still providing fluid communication between individual lines (501, 505) and the interior of reservoir (401). A cap may also prevent entrance of undesirable fluids and/or objects into the interior of reservoir (401). Additionally, it may be desirable to fix reagent supply line (501) and reagent return line (505) to a cap so that the cap may couple and decouple with the opening of reservoir (401) without twisting or entangling reagent supply line (501) and reagent return line (505) with each other. It may further be desirable to provide a cap with distinct connection features for reagent supply line (501) and reagent return line (505) in order to help prevent accidental confusion or mix-up by an operator while installing reagent supply line (501) and reagent return line (505) with the cap. Even more, it may be desirable to provide a cap with selected one-way fluid communication from the exterior of reservoir (401) to the interior of reservoir (401) to relieve a vacuum created by first pump (406) driving reagent solution away from reservoir (401), as described above.

FIGS. 5-6 and 8-9 show an exemplary reservoir cap (510) that may be readily coupled to reservoir (401). It should be understood that cap (510) may provide the features and operability referred to immediately above. Reservoir cap (510) includes a rotating body (520) and a static assembly (550). As will be described in greater detail below, rotating body (520) is capable of rotating around the circumference of static assembly (550) in order to couple reservoir cap (510) with reservoir (401). Additionally, as will be described in greater detail below, static assembly (550) is configured to couple with reagent supply line (501) and reagent return line (505) such that lines (501, 505) are in fluid communication with the interior of reservoir (401) when reservoir cap (510) is coupled with reservoir (401).

Rotating body (520) extends from a top end (521) to a bottom end (523). Rotating body (520) includes an interior surface (524) defining a hollow interior (522), a complementary threading (525) configured to couple reservoir cap (510) with threading (425) of reservoir (401), and an inwardly extending annular tab (526). Hollow interior (522) is dimensioned to house a selected portion of static assembly (550). As will be described in greater detail below, inwardly extending annular tab (526) is configured to rotatably couple rotating body (520) with static assembly (550). Additionally, as will be described in greater detail below, inwardly extended annular tab (526) is configured to press against selected portions of static assembly (550) when reservoir cap (510) is firmly coupled with reservoir (401) such that a portion of static assembly (550) creates a seal with a lip (426) of reservoir (401).

FIGS. 7A-7B show reservoir cap (510) being coupled with reservoir (401) while also being coupled with lines (501, 505). Static assembly (550) is in fluid communication with reagent supply line (501) via nut (574) and insert (576); while static assembly (550) is in fluid communication with reagent return line (505) via insert (572). Connections between lines (501, 505) and static assembly (550) will be described in greater detail below. An operator may couple reservoir cap (510) to reservoir (401) via complementary threading of rotating body (520) and threading (425) of reservoir (401). It should be understood that since rotating body (520) may rotate interpedently of static assembly (550), lines (505, 501) do not twist around each other when rotating body (520) screws onto threading (425).

Figure 8:
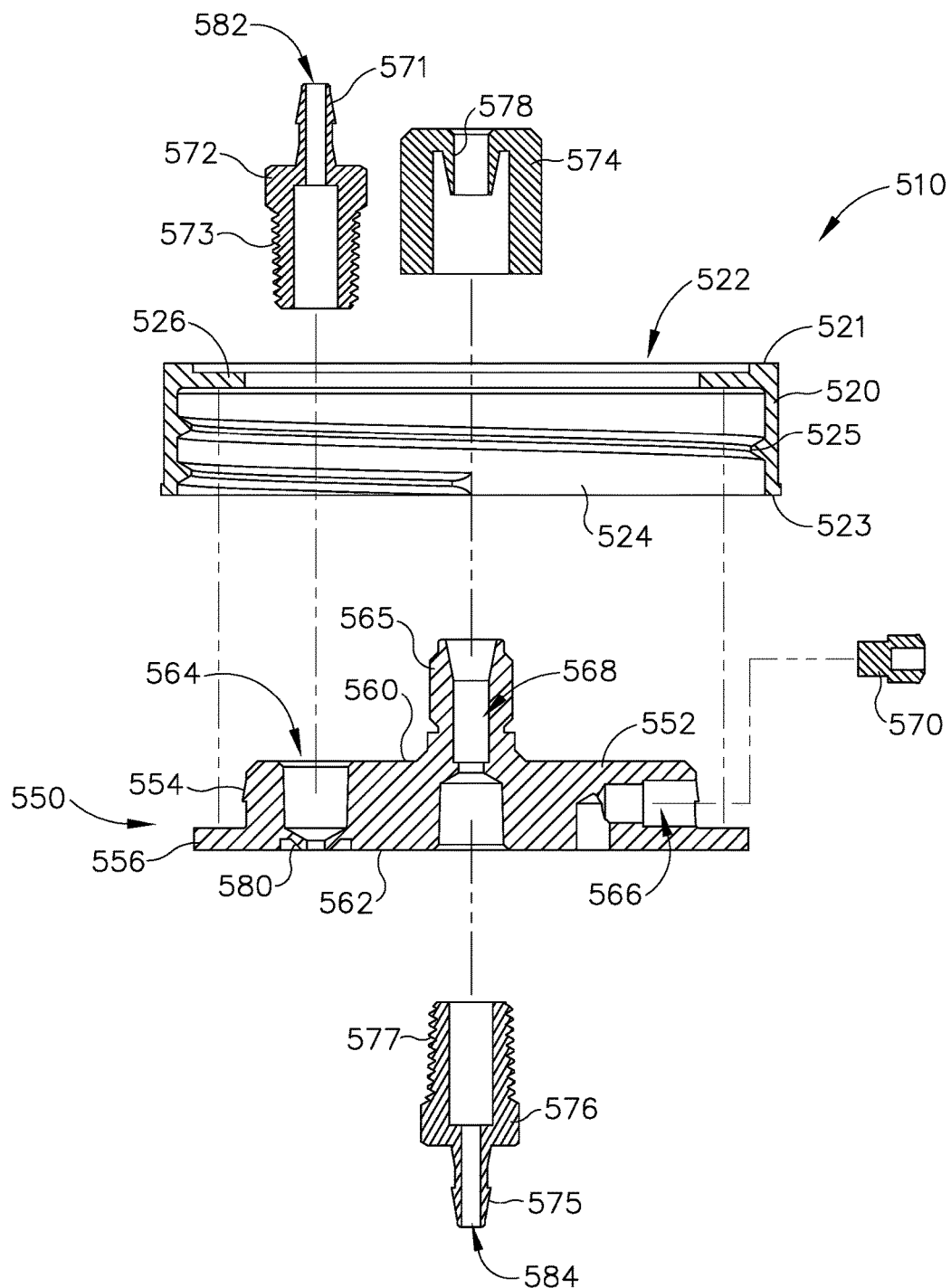
FIG. 8 depicts a cross-sectional exploded view of the reservoir cap of FIG. 5.
Figure 9:
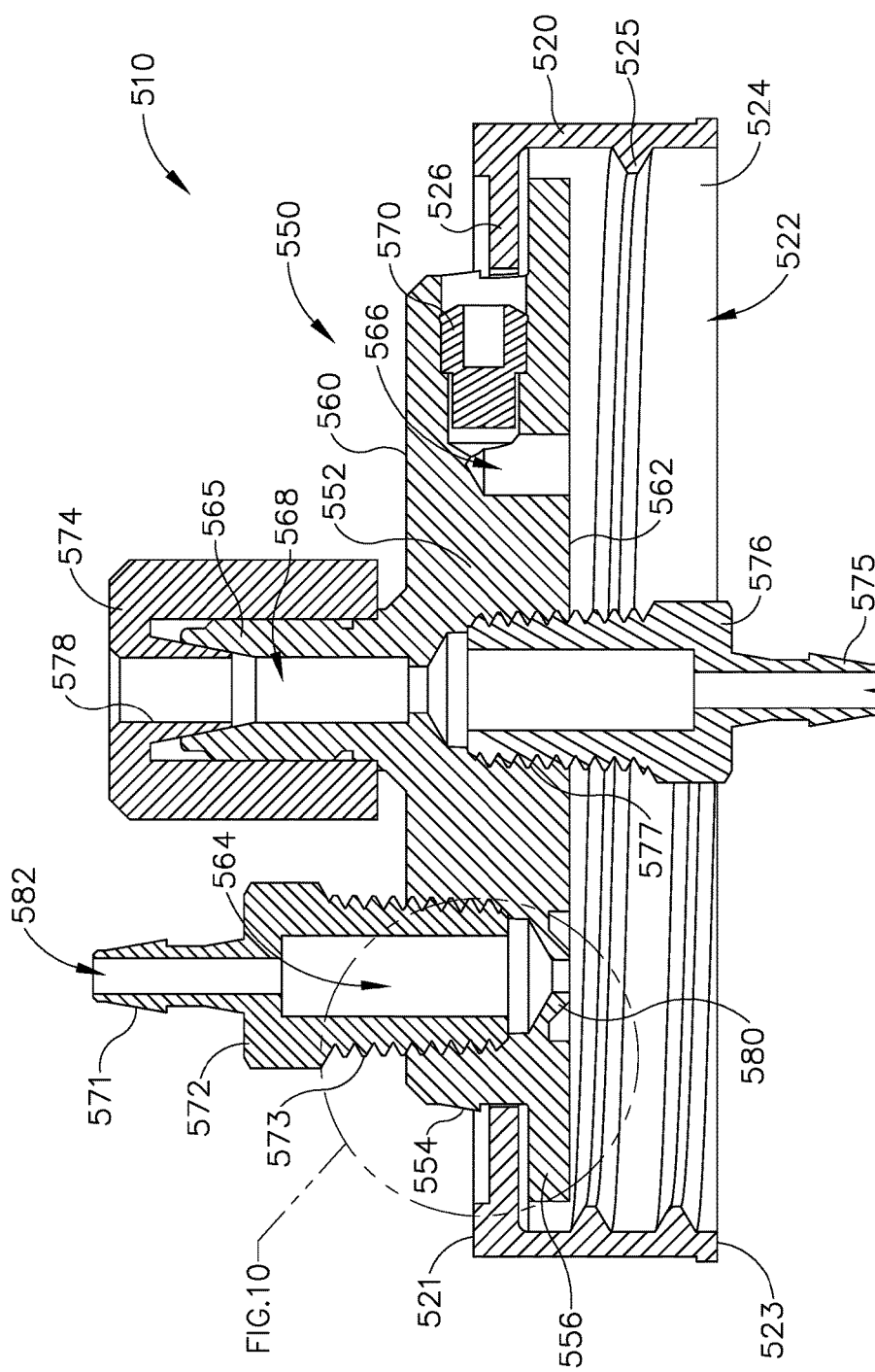
FIG. 9 depicts a cross-sectional view of the reservoir cap of FIG. 5.

As best seen in FIGS. 8-9, Static assembly (550) includes a body (552), a check valve (570), an exterior insert (572), a nut (574), and an interior insert (576). Body (552) includes an exterior surface (560) and a reservoir surface (562). Exterior surface (560) faces away from the interior of reservoir (401) when reservoir cap (510) is coupled with reservoir (401); while reservoir surface (562) faces toward the interior of reservoir (401) when reservoir cap (510) is coupled with reservoir (401). In other words, when reservoir cap (510) is coupled with reservoir (401), reservoir surface (562) associates with the interior of reservoir (401) while exterior surface (560) associates with the exterior of reservoir (401).

Figure 10:
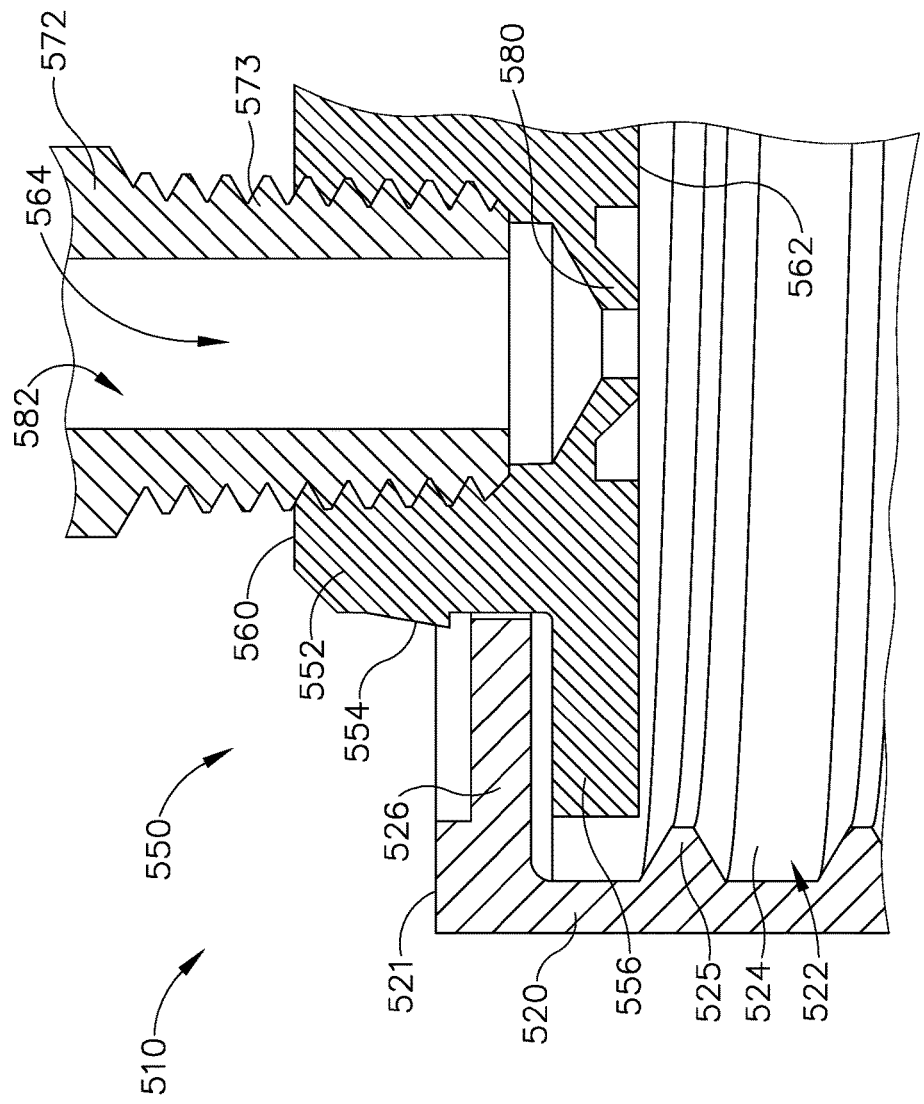
FIG. 10 depicts an enlarged cross-sectional view of a portion of the reservoir cap of FIG. 5, the enlarged portion being indicated by the circle 10 of FIG. 9.

Body (552) also includes a sloped annular surface (554), an outwardly extending annular tab (556), and an upwardly extending protrusion (565). As best shown between FIGS. 8-9, body (552) of static assembly (550) is configured to be placed within hollow interior (522) of rotating body (520) through bottom end (523). As body (552) travels through hollow interior (522), inwardly extending tabs (526) of rotating body (520) are dimensioned to abut against sloped annular surface (554) of body (552). Inwardly extending tabs (526) are sufficiently resilient to flex along sloped annular surface (554). As best shown in FIGS. 9-10, once body (552) is pushed to the point where inwardly extending tabs (526) of rotating body (520) no longer make contact with sloped annular surface (554), inwardly extending tabs (526) flex back to their relaxed position, thereby providing a snap fitting between a top surface of outwardly extending tab (556) and a bottom portion of sloped annular surface (554). Once coupled, rotating body (520) may rotate around body (552) of static assembly (550). As best seen in FIG. 10, rotating body (520) may translate in the vertical direction as constrained by inwardly extending tab (526) contacting the top surface of outwardly extending tab (556) and the bottom portion of sloped annular surface (554).

Outwardly extending annular tab (556) provides a transition from exterior surface (560) and interior surface (562). In other words, outwardly extending annular tab (556) is partially defined by both exterior surface (560) and reservoir surface (562). As described above, and will be further described below, outwardly extending annular tab (556) is configured to press against both inwardly extended annular tab (526) of rotating body (520) and lip (426) of reservoir (401) when reservoir cap (510) is firmly coupled with reservoir (401) such that outwardly extending annular tab (556) creates a seal with lip (426) of reservoir (401).

Body (552) defines a return channel (564), a check valve channel (566) and a supply channel (568), each extending from exterior surface (565) to reservoir surface (562) of body (552). Additionally, protrusion (565) also defines supply channel (568). Protrusion (565) is dimensioned to mate with nut (574) in order to form a fluid right seal. Additionally, nut (578) defines an inner diameter configured for an interference fit with the outer diameter of the portion of reagent supply line (501) extending above reservoir cap (510), also forming a fluid tight seal. Therefore, nut (578) may mate with protrusion (565) of body (552) and supply channel (568) in order to establish fluid communication between reservoir (401), reagent supply line (501), and supply channel (568).

Exterior insert (572) and interior insert (576) each include a barbed mating feature (571, 575) and a threaded region (573, 577), respectively. The outer diameter of barbed mating feature (571) is dimensioned for an interference fit with the inner diameter of reagent return line (505). Therefore, the outer diameter of reagent return line (505) may be dimensioned either too large or too small for an interference fit with inner diameter (578) of nut (574); while the inner diameter of reagent supply line (501) may be dimensioned either too small or too large for an interference fit with barbed mating feature (571) of insert (572). These features may serve a poka-yoke purpose preventing an operator from accidentally mixing up the connection between nut (574) and reagent supply line (501); and the connection between inset (572) and reagent return line (505).

Interior insert (576) is substantially similar to exterior insert (572), except that interior insert (576) connects the portion of reagent supply line (501) within reservoir (401) to supply channel (568). Therefore, the outer diameter of barbed mating feature (575) is dimensioned for an interference fit with the inner diameter of the portion of reagent supply line (505) extending within reservoir (401).

Inserts (572, 576) each define a respective fluid channel (582, 584). Threaded regions (573, 577) may couple inserts (572, 576) with their respective channels (564, 568) with a fluid tight seal such that fluid may not escape between threaded regions (573, 577) and channels (564, 568). A fluid tight seal may be provided by any suitable manner known to one having ordinary skill in the art in view of the teachings herein. Additionally, body (552) includes a fluid break (580) located within return channel (564) and adjacent to reservoir surface (562). Fluid break (580) may help prevent an excess accumulation of fluid to accumulate within return channel (564), therefore helping further ensure a fluid tight seal between threaded region (573) and return channel (564). In particular, fluid break (580) may ensure that liquid passing through return channel (564) will only flow into reservoir (401), without leaking out through the interface between threading (525) on surface (524) of rotating body (520) and threading (425) of reservoir (401). Such leaking might otherwise occur if rotating body (520) is not fully tightened. Fluid break (580) may thus prevent such leakage.

As can be seen among FIGS. 8-9, check valve (570) may be inserted into check valve channel (570) defined by body (552). The exterior of check valve (570) may provide a fluid tight seal against check valve channel (570). Check valve (570) may be affixed to body with a fluid tight seal via an interference fit or any other suitable coupling features as would be apparent to one having ordinary skill in the art in view of the teachings herein. It should be understood that since check valve (570) and check valve channel (570) are connected with a fluid tight seal, fluid communication between exterior surface (560) and reservoir surface (562) via check value channel (566) is limited to that dictated by check valve (570). Check valve (570) may be configured as a one-way valve allowing air to enter the interior of reservoir (401) to relive the vacuum created by pump (406) as described above. Therefore, check valve (570) may prevent fluids from escaping reservoir (401) via check value (570).

Figure 11A:
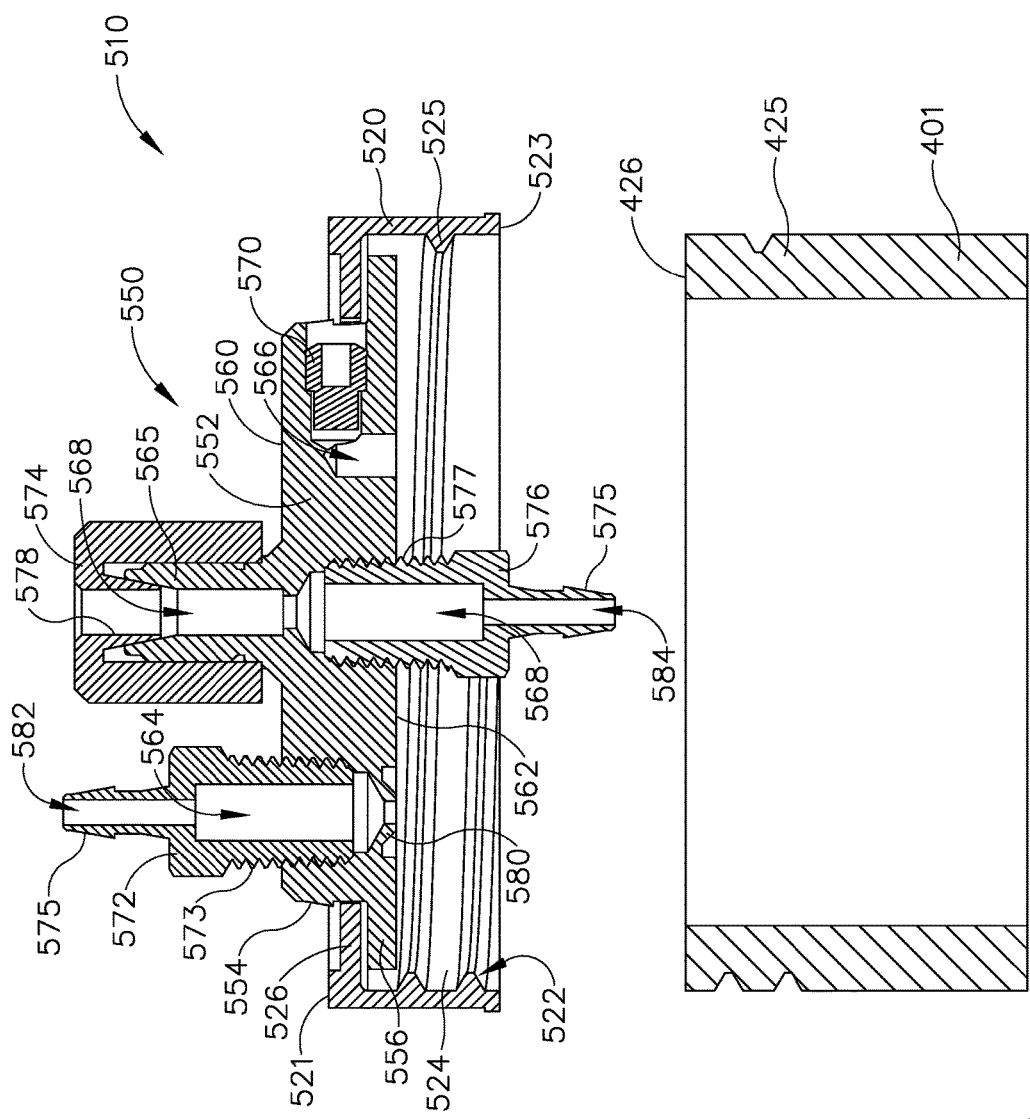
FIG. 11A depicts a cross-sectional view of the reservoir cap of FIG. 5 placed above the fluid reservoir of the disinfectant concentration measuring subsystem of FIG. 4.

FIGS. 11A-12B show an exemplary coupling of reservoir cap (510) with reservoir (401). It should be understood that lines (501, 505) have been omitted from FIGS. 11A-12B for purposes of clarity. FIG. 11A shows an assembled reservoir cap (510) placed over of open lip (426) of reservoir (401).

Figure 11B:
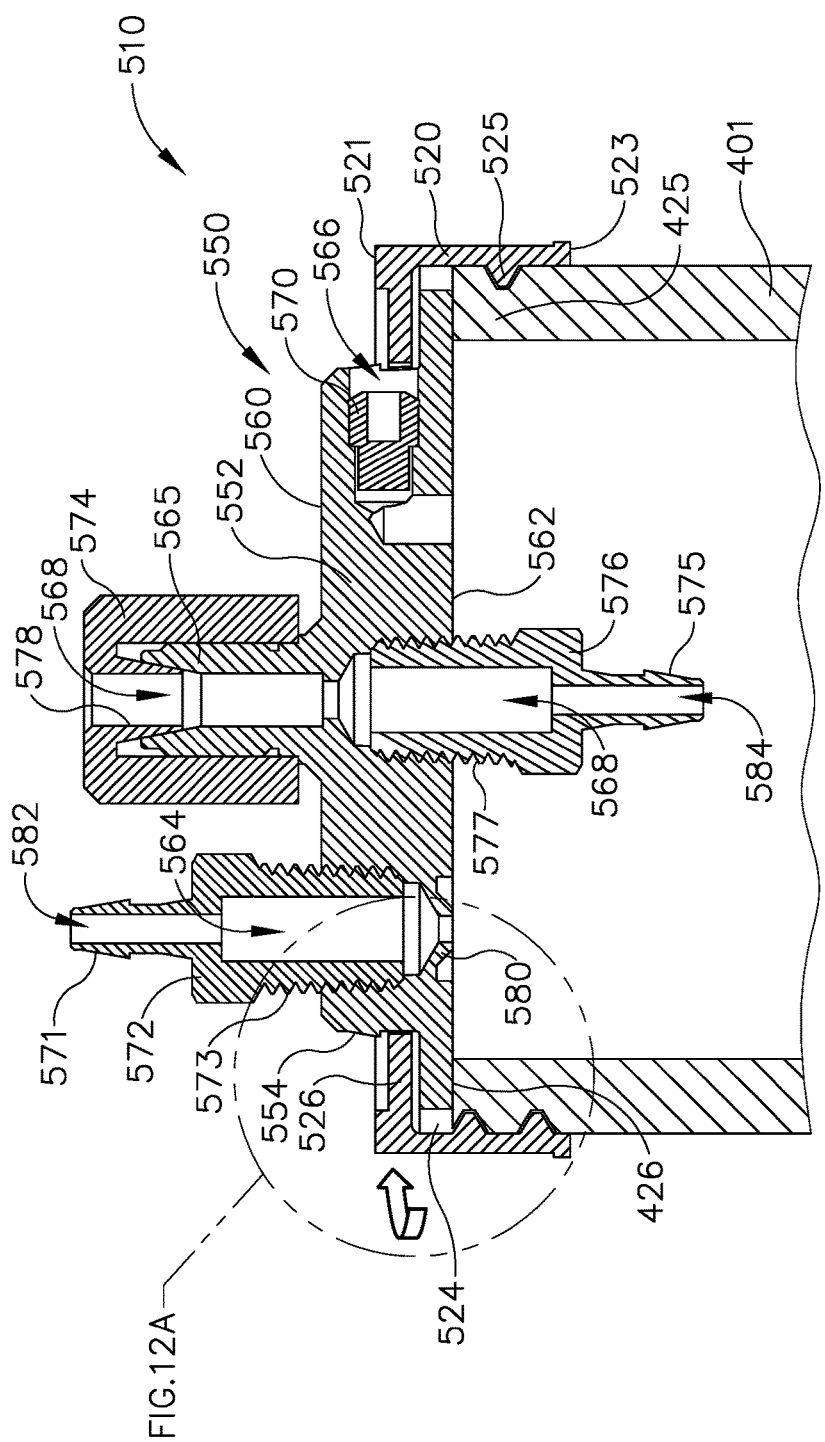
FIG. 11B depicts a cross-sectional view of the reservoir cap of FIG. 6 partially coupled with the fluid reservoir of the disinfectant concentration measuring subsystem of FIG. 4, where a rotating body of the reservoir cap is coupled with the fluid reservoir while the rotating body is not in contact with a static assembly of the reservoir cap.
Figure 12A:
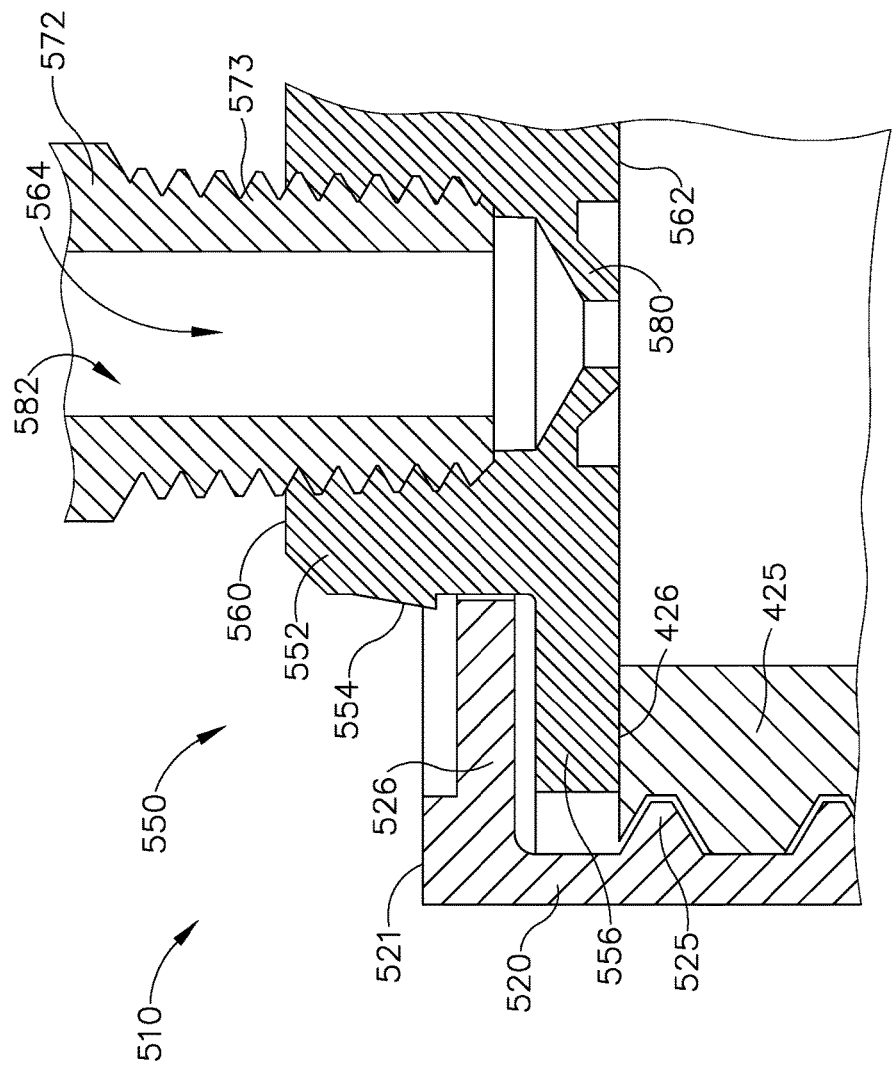
FIG. 12A depicts an enlarged cross-sectional view of a portion of the reservoir cap of FIG. 6 partially coupled with the fluid reservoir of the disinfectant concentration measuring subsystem of FIG. 4, where the rotating body of the reservoir cap is coupled with the fluid reservoir while the rotating body is not in contact with the static assembly of the reservoir cap, the enlarged portion being indicated by the circle 12A of FIG. 11B.

Next, as shown in FIGS. 11B and 12A, a user may rotate rotating body (520) relative to both static assembly (550) and reservoir (401) such that complementary threads (525) of rotating body (520) engage threading (425) of reservoir (401). It should be understood that because rotating body (520) is capable of translating along a predefined distance relative to static assembly (550) as described above, rotating body (520) may be rotated such that outwardly extending tabs (556) rest against lip (426) while inwardly extending tab (526) of rotating body (520) does not engage outwardly extending tab (556). Therefore, at the point shown in FIGS. 11B and 12A, outwardly extending tab (556) may not press against open lip (426) with enough force to ensure a fluid tight seal.

Figure 12B:
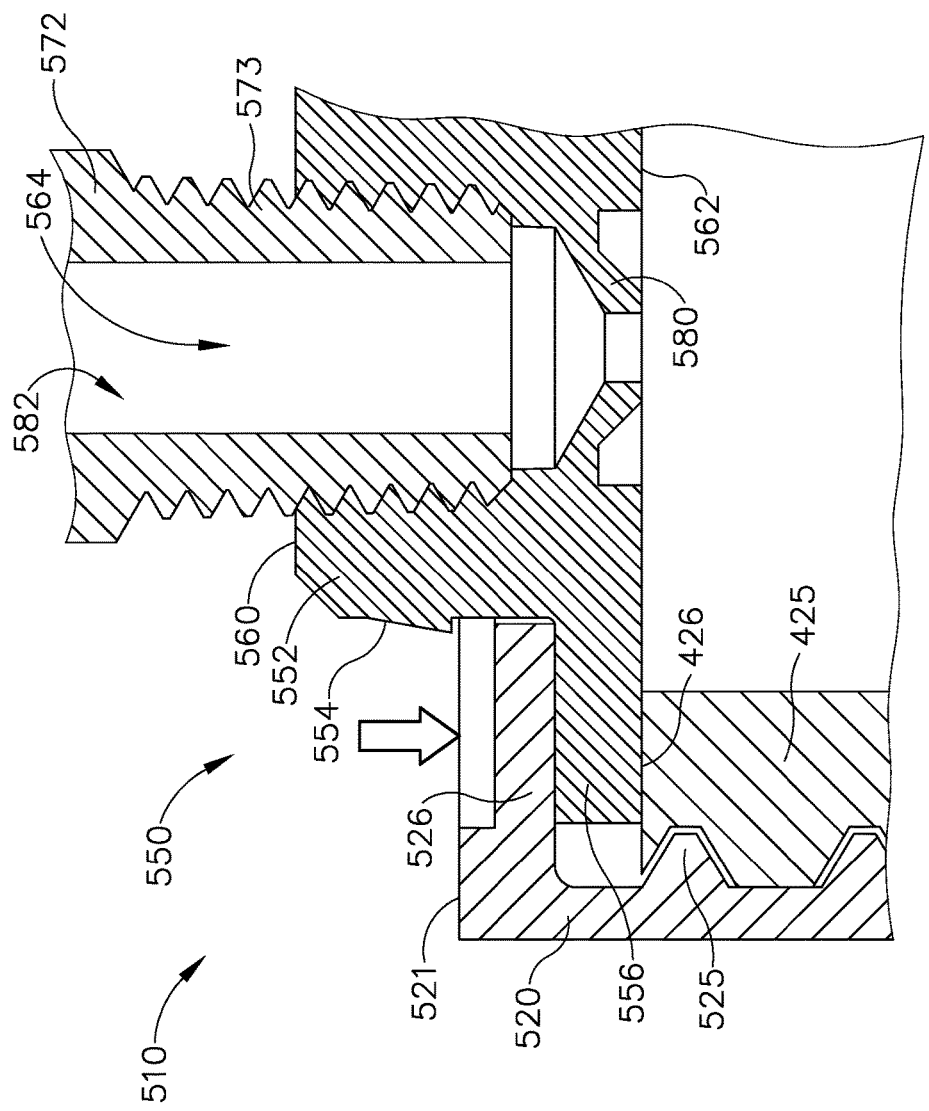
FIG. 12B depicts an enlarged cross-sectional view of a portion of the reservoir cap of FIG. 6 fully coupled with the fluid reservoir of the disinfectant concentration measuring subsystem of FIG. 4, where the rotating body of the reservoir cap is coupled with the fluid reservoir while the rotating body is also in contact with the static assembly of the reservoir cap, the enlarged portion being indicated by the circle 12B of FIG. 11C.

A user may further rotate rotating body (520) such that complementary threads (525) further engage threading (425) of reservoir (401). As shown in FIGS. 11C and 12B, further rotation a rotating body (520) may also translate inwardly extending tab (526) toward outwardly extending tab (556), forcing inwardly extending tab (526) into engagement with outwardly extending tab (556), effectively acting as a clamp. With outwardly extending tab (556) clamped against both open lip (426) and inwardly extending tab (526) due to rotatable engagement of threads (525, 425) translating rotating body (520) toward reservoir (401), a fluid tight seal may be created between outwardly extending tab (556) and open lip (426).

It should be understood from the foregoing that, when reservoir cap (510) is properly attached to reservoir (401), fluid communication between external surface (560) and reservoir surface (562) is limited to return channel (564), supply channel (568), and check valve channel (566). It should also be understood that, during rotation of rotating body (520), lines (501, 505) and static assembly (550) may remain stationary, as not to twist or entangle lines (501, 505) with each other.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A medical device processor comprising: (a) an enclosure for holding a medical device; (b) a liquid distribution system configured to deliver a disinfectant solution to a medical device within the enclosure, the liquid distribution system comprising a liquid outlet; and (c) a disinfectant concentration measuring subsystem comprising: (i) a first mixing chamber in fluid communication with the liquid outlet, (ii) a reservoir configured to contain a reagent solution, wherein the reservoir is in fluid communication with the first mixing chamber, (iii) a reservoir cap configured to couple with the reservoir, wherein the reservoir cap comprises: (A) a static member configured to couple with a supply conduit and a return conduit, and (B) a rotating member configured to rotate relative to the static member to couple the reservoir cap with the reservoir, (iv) a pump that is configured to simultaneously pump the disinfectant solution and the reagent solution into the first mixing chamber, and (v) a concentration analysis assembly that is operable to determine a concentration of disinfectant in a sample solution that is output from the first mixing chamber.

Example 2

The medical device processor of Example 1, wherein the reservoir is in fluid communication with the pump via the supply conduit.

Example 3

The medical device processor of Example 2, further comprising a valve in communication with the pump and the return conduit.

Example 4

The medical device processor of any one or more of Examples 1 through 3, wherein the static member comprises a first insert and a second insert, wherein the supply conduit is configured to couple with the first insert, wherein the return conduit is configured to couple with the second insert.

Example 5

The medical device processor of Example 4, wherein the first insert comprises a nut, wherein the second insert comprises a barbed fitting feature.

Example 6

The medical device processor of Example 5, wherein the second insert further comprises a threaded region, wherein the threaded region is configured to fix the second insert to a body of the static member.

Example 7

The medical device processor of Example 6, wherein the threaded region and the body of the static member together form a fluid tight seal.

Example 8

The medical device processor of any one or more of Examples 1 through 7, further comprising a feed conduit housed within the reservoir, wherein the feed conduit is connected to the static member, wherein the feed conduit is in communication with supply conduit.

Example 9

The medical device processor of any one or more of Examples 1 through 8, wherein the rotating member comprises a first threading, wherein the reservoir comprises a second threading, wherein the rotating member is configured to couple with reservoir via the first threading and the second threading.

Example 10

The medical device processor of Example 9, wherein the static member comprises a first circumferential tab, wherein the rotating member comprises a second circumferential tab, wherein the second circumferential tab is configured to push the first circumferential tab against the reservoir to create a fluid tight seal with the static member and the reservoir.

Example 11

The medical device processor of any one or more of Examples 1 through 10, wherein the static member further comprises a check valve configured to allow air within the reservoir.

Example 12

The medical device processor of any one or more of Examples 1 through 11, wherein the static member further comprises a sloped annular surface, wherein the rotating member comprises a resilient tab, wherein the rotating member is configured to snap fit over the sloped annular surface to rotatably couple the rotating member with the static member.

Example 13

The medical device processor of any one or more of Examples 1 through 12, wherein the pump comprises a dual-head stepper motor.

Example 14

The medical device processor of any one or more of Examples 1 through 13, wherein the pump is configured to simultaneously pump the disinfectant solution and the reagent solution at volumetric flow rate ratio of about 1:1.

Example 15

The medical device processor of any one or more of Examples 1 through 14, wherein the static member further comprises a fluid break in fluid communication with the return conduit.

Example 16

The medical device processor of Example 15, wherein the static member further comprises an insert located between the fluid break and the return conduit.

Example 17

A disinfectant concentration measuring subsystem comprising: (a) a reservoir configured to contain a reagent solution, wherein the reservoir comprises an open end; (b) a reservoir cap configured to couple with the open end of the reservoir, wherein the reservoir cap comprises: (i) a static member configured to couple with a supply conduit and a return conduit, and (ii) a moving member associated with the static member, wherein the moving member is configured to move relative to the static member to couple with the open end of the reservoir; (c) a pump configured to pump the reagent solution from the reservoir through the return conduit; (d) a valve in communication with the pump and the return conduit, wherein the valve is configured to selectively pump reagent solution back into the reservoir via the return conduit; and (e) a concentration analysis assembly that is operable to receive a disinfectant solution and the reagent solution.

Example 18

The disinfectant concentration measuring subsystem of Example 17, wherein the moving member is configured to translate and rotate relative to the static member.

Example 19

The disinfectant concentration measuring subsystem of Example 18, wherein the moving member comprises a tab encompassing the static member, wherein the tab is configured to vertically slide relative to the static member while simultaneously rotating relative to the static member.

Example 20

A reservoir cap assembly configured to couple with a reservoir, wherein the reservoir cap assembly is configured to provide fluid communication with a pump and a valve, wherein the valve and the pump are in fluid communication with each other, wherein the reservoir cap assembly comprises: (a) a static member comprising: (i) a body defining a return channel and a supply channel, (ii) a supply conduit in fluid communication with the supply channel, wherein the supply conduit is in fluid communication with the pump, and (iii) a return conduit in fluid communication with the return channel and the valve; and (b) a rotating member configured to rotate relative to the static member to couple the reservoir cap with the reservoir.

VI. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A medical device processor comprising:
   (a) an enclosure for holding a medical device;
   (b) a liquid distribution system configured to deliver a disinfectant solution to a medical device within the enclosure, the liquid distribution system comprising a liquid outlet; and
   (c) a disinfectant concentration measuring subsystem comprising:
      (i) a first mixing chamber in fluid communication with the liquid outlet,
      (ii) a reservoir configured to contain a reagent solution, wherein the reservoir is in fluid communication with the first mixing chamber,
      (iii) a reservoir cap configured to couple with the reservoir, wherein the reservoir cap comprises:
         (A) a static member defining a first fluid channel and a second fluid channel,
         (B) a supply conduit in fluid commination with the first fluid channel,
         (C) a return conduit in fluid communication with the second fluid channel, and
         (D) a rotating member configured to rotate relative to the static member such that the supply conduit and the return conduit do not twist relative to the static member, wherein rotation of the rotating member relative to the static member is configured to couple the reservoir cap with the reservoir; and (iv) a pump assembly that is configured to simultaneously pump the disinfectant solution and the reagent solution into the first mixing chamber.

2. The medical device processor of claim 1, wherein the reservoir is in fluid communication with the pump assembly via the supply conduit.

3. The medical device processor of claim 2, further comprising a valve in communication with the pump assembly and the return conduit.

4. The medical device processor of claim 1, wherein the static member comprises a first insert and a second insert, wherein the supply conduit is configured to couple with the first insert, wherein the return conduit is configured to couple with the second insert.

5. The medical device processor of claim 4, wherein the first insert comprises a nut, wherein the second insert comprises a barbed fitting feature.

6. The medical device processor of claim 5, wherein the second insert further comprises a threaded region, wherein the threaded region is configured to fix the second insert to a body of the static member.

7. The medical device processor of claim 6, wherein the threaded region and the body of the static member together form a fluid tight seal.

8. The medical device processor of claim 1, further comprising a feed conduit housed within the reservoir, wherein the feed conduit is connected to the static member, wherein the feed conduit is in communication with supply conduit.

9. The medical device processor of claim 1, wherein the rotating member comprises a first threading, wherein the reservoir comprises a second threading, wherein the rotating member is configured to couple with reservoir via the first threading and the second threading.

10. The medical device processor of claim 9, wherein the static member comprises a first circumferential tab, wherein the rotating member comprises a second circumferential tab, wherein the second circumferential tab is configured to push the first circumferential tab against the reservoir to create a fluid tight seal with the static member and the reservoir.

11. The medical device processor of claim 1, wherein the static member further comprises a check valve configured to allow air within the reservoir.

12. The medical device processor of claim 1, wherein the static member further comprises a sloped annular surface, wherein the rotating member comprises a resilient tab, wherein the rotating member is configured to snap fit over the sloped annular surface to rotatably couple the rotating member with the static member.

13. The medical device processor of claim 1, wherein the pump assembly comprises a dual-head stepper motor.

14. The medical device processor of claim 1, wherein the pump assembly is configured to simultaneously pump the disinfectant solution and the reagent solution at volumetric flow rate ratio of about 1:1.

15. The medical device processor of claim 1, wherein the static member further comprises a fluid break in fluid communication with the return conduit.

16. The medical device processor of claim 15, wherein the static member further comprises an insert located between the fluid break and the return conduit.

17. The medical device processor of claim 1, wherein the disinfectant concentration measuring subsystem further comprises a concentration analysis assembly that is operable to determine a concentration of disinfectant in a sample solution that is output from the first mixing chamber.

18. A medical device processor comprising:
(a) an enclosure for holding a medical device;
(b) a liquid distribution system configured to deliver a disinfectant solution to a medical device within the enclosure, the liquid distribution system comprising a liquid outlet; and
(c) a disinfectant concentration measuring subsystem comprising:
(i) a first mixing chamber in fluid communication with the liquid outlet,
(ii) a reservoir comprising an external threading, wherein the reservoir is configured to contain a reagent solution, wherein the reservoir is in fluid communication with the first mixing chamber,
(iii) a reservoir cap configured to couple with the reservoir, wherein the reservoir cap comprises:
(A) a static member defining a first fluid pathway and a second fluid pathway, wherein the first fluid pathway is configured to couple with a supply conduit, wherein the second fluid pathway is configured to couple with a return conduit, and
(B) a rotating member comprising an internal threading configured to couple with the external threading of the reservoir, wherein the rotating member is configured to rotate relative to the static member and the reservoir to couple the reservoir cap with the reservoir, wherein the first fluid pathway and the second fluid pathway are in fluid communication with the reservoir when the reservoir cap is coupled with the reservoir; and
(iv) a pump assembly that is configured to simultaneously pump the disinfectant solution and the reagent solution into the first mixing chamber.

19. A medical device processor comprising:
(a) an enclosure for holding a medical device;
(b) a liquid distribution system configured to deliver a disinfectant solution to a medical device within the enclosure, the liquid distribution system comprising a liquid outlet; and
(c) a disinfectant concentration measuring subsystem comprising:
(i) a first mixing chamber in fluid communication with the liquid outlet,
(ii) a reservoir comprising an interior and an external coupling feature, wherein the interior of the reservoir is configured to contain a reagent solution, wherein the reservoir is in fluid communication with the first mixing chamber,
(iii) a reservoir cap configured to couple with the reservoir, wherein the reservoir cap comprises:
(A) a static member defining a first fluid pathway and a second fluid pathway, wherein the first fluid pathway is configured to couple with a supply conduit, wherein the second fluid pathway is configured to couple with a return conduit, and
(B) a rotating member configured to rotate relative to the static member and the reservoir to couple with the external coupling feature of the reservoir, wherein the first fluid pathway and the second fluid pathway of the static member are in fluid communication with the interior of the reservoir when the rotating member is coupled with the external coupling feature of the reservoir; and (iv) a pump assembly that is configured to simultaneously pump the disinfectant solution and the reagent solution into the first mixing chamber.

\* \* \* \* \*